US006372888B1

(12) United States Patent
De Samblanx et al.

(10) Patent No.: US 6,372,888 B1
(45) Date of Patent: Apr. 16, 2002

(54) ANTIFUNGAL PROTEINS

(75) Inventors: Genoveva Wivina De Samblanx, Heverlee; Willem Frans Broekaert, Dilbeek, both of (BE); Sarah Bronwen Rees, Bracknell (GB)

(73) Assignee: Zeneca Limited, London (GB)

( * ) Notice: Subject to any disclaimer, the term of this patent is extended or adjusted under 35 U.S.C. 154(b) by 0 days.

(21) Appl. No.: 09/077,951

(22) PCT Filed: Dec. 12, 1996

(86) PCT No.: PCT/GB96/03065

§ 371 Date: Mar. 11, 1999

§ 102(e) Date: Mar. 11, 1999

(87) PCT Pub. No.: WO97/21814

PCT Pub. Date: Jun. 19, 1997

(30) Foreign Application Priority Data

Dec. 13, 1995 (GB) ............................................. 9525474

(51) Int. Cl.[7] ................................................. C07K 1/00

(52) U.S. Cl. ...................... 530/350; 530/350; 530/300; 530/324; 800/301; 800/302; 800/DIG. 9; 435/7.2; 435/7.31; 435/320.1; 435/172.3; 435/419; 514/12; 536/23.6

(58) Field of Search .................................. 530/350, 324, 530/300; 424/1.69, 439; 800/301, 302, DIG. 9; 435/7.2, 7.31, 320.01, 419, 172.3; 536/23.6; 514/12

(56) References Cited

U.S. PATENT DOCUMENTS 5,919,918 A * 7/1999 Broekaert et al. ......... 536/23.6

FOREIGN PATENT DOCUMENTS

| WO | WO87/03303 | 6/1987 |
| WO | WO90/13224 | 11/1990 |
| WO | WO93/05153 | 3/1993 |
| WO | WO93/10363 | 5/1993 |
| WO | WO94/16076 | 7/1994 |
| WO | WO 94/16076 | * 7/1994 |

OTHER PUBLICATIONS

Alignments (SEQ ID No. 9).*
Elble, R., "A Simple and Efficient Procedure for Transformation of Yeasts", BioTechniques, BioFeedback, vol. 13, No. 1, pp. 18–20, 1992.
Terras, FRG et al., "Analysis of Two Novel Classes of Plant Antifungal Proteins from Radish (*Raphanus sativus* L) Seeds", Journal of Biological Chemistry, vol. 267, pp. 15301–15309, 1992.
Terras, FRG et al., "A new family of basic cysteine–rich plant antifungal proteins from Brassicaceae species", FEBS Lett, vol. 316, No. 3, pp. 233–240, 1993.
Terras, FRG et al., "Small Cysteine–Rich Antifungal Proteins from Radish: Their Role in Host Defense", Plant Cell, vol. 7, pp. 573–588, 1995.
Broekaert et al., "Plant Defensins: Novel Antimicrobial Peptides as Components of the Host Defense System", Plant Physiol, vol. 108, pp. 1353–1358, 1995.
Vilas Alves, A.L. et al., "Expression of functional *Raphanus sativus* antifungal protein in yeast", FEBS Lett, vol. 348, pp. 228–232, 1994.
Macklon, A.E.S., "Calcium fluxes at plasmalemma and tonoplast", Plant Cell Environ, vol. 7, pp. 407–413, 1984.
Hepler and Wayne, "Calcium and Plant Development", Ann Rev Plant Physiol, vol. 36, pp. 397–439, 1985.
Harker and Venis, "Measurement of intracellular and extracellular free calcium in apple fruit cells using calcium–selective microelectrodes", Plant Cell Environ, vol. 14, pp. 525–530, 1991.
Bennetzen and Hall, "Codon Selection in Yeast", Journal of Biological Chemistry, vol. 257, No. 6, pp. 3026–3031, 1982.
Reichhart, JM et al., Invertebrate Reproduction and Development, vol. 21, No. 1, pp. 15–24, 1992.
Sherman, F., "Getting Started with Yeast", Methods in Enzymology, vol. 194, pp. 3–21, 1991.
Ward, A.C., "Single step purification of shuttle vectors from yeast for high frequency back–transformation into *E. coli*", Nucleic Acids Resarch, vol. 18, No. 17, p. 5319, 1990.
Broekaert et al., "An automated quantitative assay for fungal growth inhibition", FEMS Microbiology Lett, vol. 69, pp. 55–60, 1990.
Bloch and Richardson, FEBS Lett, vol. 279, No. 1, pp. 101–104, 1991.
Merino et al., "A General PCR–Based Method for Single or Combinatorial Oligonucleotide–Directed Mutagenesis on pUC/M13 Vectors", BioTchniques, BioFeedback, vol. 12, No. 4, pp. 508–510, 1992.
Osborn, RW et al., "Isolation and characterisation of plant defensins from seeds of Asteraceae, Fabaceae, Hippocastanaceae and Saxifragaceae", FEBS Letters, vol. 368, No. 2, pp. 257–262, 1995.
Rees, SB et al., "Plant antifungal proteins: novel crop protection agents", in G.K. Dixon et al. editors, *Antifungal Agents: Discovery Mode Action*, Bios Scientific Publishers, Oxford, United Kingdom, chap. 16, pp. 193–200, 1995.
Lin, Zhong–ping et al., "Conservation of Plant Genes, Screening Valuables Genes from Wild Species of Plants", in R.P. Adams and J.E. Adams, editors, *Conservation of Plant Genes*, Academic Press, San Diego, California, pp. 241–246, 1992.

(List continued on next page.)

Primary Examiner—Karen Cochrane Carlson
Assistant Examiner—Hope A. Robinson
(74) Attorney, Agent, or Firm—Hale and Dorr LLP

(57) ABSTRACT

Antifungal proteins which are analogues of the Rs-AFP2 protein and contain particular mutations in their amino acid sequence. The mutated proteins possess enhanced salt-tolerant antifungal activity. The proteins are useful for combating fungal diseases in agricultural, pharmaceutical or preservative applications.

5 Claims, 8 Drawing Sheets

OTHER PUBLICATIONS

Cornelissen, BJC et al., "Strategies for control of Fungal Diseases with Transgenic Plants", Plant Physiology, vol. 101, pp. 709–712, 1993.

Broekaert, WF et al., "Antifungal Proteins and Their Application in the Molecular Breeding of Disease–Resistant Plants", ACTA Horticulturae, No. 355, pp. 209–211, 1994.

De Samblanx, GW et al., "Antifungal Activity of synthetic 15–mer Peptides Based on the Rs–AFP2 (*Raphanus sativus* antifungal protein 2) Sequence", Peptide Research, vol. 9, No. 6, pp. 262–268, 1996.

De Samblanx GW et al., "Mutational Analysis of a Plants Defensin from Radish (*Raphanus sativus* L.) Reveals Two Adjacent Sites Important for Antifungal Activity", Journal of Biological Chemistry, vol. 272 No. 2, pp. 1171–1179, 1997.

* cited by examiner

Fig.1.

```
            1             11             21          31            41          51
Rs-AFP1   QKLCERPSGT   WSGVCGNNNA   CKNQCINLEK   ARHGSCNYVF   PAHKCICYFP   C
Rs-AFP2   QKLCQRPSGT   WSGVCGNNNA   CKNQCIRLEK   ARHGSCNYVF   PAHKCICYFP   C
Rs-AFP3   -KLCERSSGT   WSGVCGNNNA   CKNQCIRLEG   AQHGSCNYVF   PAHKCICYFP   C
Rs-AFP4   QKLCERSSGT   WSGVCGNNNA   CKNQCINLEG   ARHGSCNYIF   PYHRCICYFP   C
Br-AFP1   QKLCERPSGT   WSGVCGNNNA   CKNQCIN
Br-AFP2   QKLCERPSGT   ?SGVCGNNNA   CKNQCIR
Bn-AFP1   QKLCERPSGT   WSGVCGNNNA   CKNQCINLEK
Bn-AFP2   QKLCERPSGT   WSGVCGNNNA   CKN
Sa-AFP1   QKLCERPSGT   WSGVCGNNNA   CKNQC
Sa-AFP2   QKLCQRPSGT   WSGVCGNNNA   CRNQCI
At-AFP1   QKLCERPSGT   WSGVCGNSNA   CKNQCIN
```

Fig.2.

```
GTTTTATTAGTGATCATGGCTAAGTTTGCGTCCATCATCGCACTT      45
                 M  A  K  F  A  S  I  I  A  L

CTTTTTGCTGCTCTTGTTCTTTTTGCTGCTTGTCGAAGCACCAACA      90
 L  F  A  A  L  V  L  F  A  A  F  E  A  E  T

ATGGTGGAAGCACAGAAGTTGTGCGAAAGGCCAAGTGGGACATGG     135
 M  V  E  A  Q  K  L  C  E  R  P  S  G  T  W

TCAGGAGTCTGTGTGGAAACAATAACGCATGCAAGAATCAGTGCATT    180
 S  G  V  C  G  N  N  N  A  C  K  N  Q  C  I

AACCTTGAGAAAGCACGACATGGATCTTGCAACTATGTCTTCCCA     225
 N  L  E  K  A  R  H  G  S  C  N  Y  V  F  P

GCTCACAAGTGTATCTGCTACTTTCCTTGTAATTTATCGCAAAC     270
 A  H  K  C  I  C  Y  F  P  C  *

TCTTTGGTGAATAGTTTTTATGTAATTTACACAAAATAAGTCAGT     315

GTCACTATCCATGAGTGATTTTAAGACATGTACCAGATATGTTAT     360

GTTGGTTCGGTTATACAAATAAAGTTTATTCACCAAAAAAAAAA     405

AAAAAAAAA                                        414
```

Fig.4.

```
                 1        10        20        30        40        50
                 |        |         |         |         |         |
Rs-AFP2          ZKLCQRPSGTWSGVCGNNNACKNQCIRLEKARHGSCNYVFPAHKCICYFPC
yRs-AFP2         Q..................................................
SIα2             -RV.MKG.AGFK.L.MRDQN.AQV.L-Q.GWGG.N.DG.M--RQ.K.IRQ.
SERIES A
yRs-AFP2/Q5M     Q...M..............................................
yRs-AFP2/T10G    Q........G.........................................
yRs-AFP2/W11S    Q.........S........................................
yRs-AFP2/G16M    Q..............M...................................
yRs-AFP2/A31W    Q.............................W....................
yRs-AFP2/Y38G    Q....................................G.............
yRs-AFP2/F40M    Q......................................M...........
yRs-AFP2/K44Q    Q..........................................Q.......
yRs-AFP2/Y48I    Q..............................................I...
SERIES B
yRs-AFP2/T10A    Q........A.........................................
yRs-AFP2/H33A    Q...............................A..................
yRs-AFP2/Y38A    Q....................................A.............
yRs-AFP2/F40A    Q......................................A...........
SERIES C
yRs-AFP2/P7-     Q.....-............................................
yRs-AFP2/P41-    Q....................................... ..........
SERIES D
yRs-AFP2/P7R     Q.....R............................................
yRs-AFP2/G9R     Q.......R..........................................
yRs-AFP2/S12R    Q..........R.......................................
yRs-AFP2/I26R    Q........................R.........................
yRs-AFP2/L28R    Q..........................R.......................
yRs-AFP2/N37R    Q...................................R..............
yRs-AFP2/V39R    Q.....................................R............
yRs-AFP2/A42R    Q........................................R.........
yRs-AFP2/I46R    Q............................................R.....
yRs-AFP2/F49R    Q...............................................R..
```

FIG. 5A

OWB41: <u>AATAAGCTTTGGACAAGAGA</u>

| | $^1$Q | $^2$K | $^3$L | $^4$C | $^5$Q | $^6$R | $^7$P | |
|---|---|---|---|---|---|---|---|---|
| | CAG | AAG | TTG | TGC | CAA | AGG | CCA | AG |
| | CAG | AAG | TTG | TGC | ATG | AGG | CCA | AG |
| | Q | K | L | C | M | R | P | |

| | $^3$L | $^4$C | $^5$Q | $^6$R | $^7$P |
|---|---|---|---|---|---|
| OWB42: | TTG | TGC | CAA | AGG | CCA |
| | TTG | TGC | CAA | AGG | --- |
| | L | C | Q | R | - |

| | $^7$P | $^8$S | $^9$G | $^{10}$T | $^{11}$W | |
|---|---|---|---|---|---|---|
| OWB43: | CCA | AGT | GGG | ACA | TGG | |
| | CCA | AGT | GGG | ACA | TGG | |
| | P | S | G | T | W | |

| | $^8$S | $^9$G | $^{10}$T | $^{11}$W | $^{12}$S | |
|---|---|---|---|---|---|---|
| | AGT | GGG | ACA | TGG | TCA | GG |
| | AGT | GGG | GGT | TCC | TCA | GG |
| | S | G | G | S | S | |

| | $^{13}$G | $^{14}$V | $^{15}$C | $^{16}$G | $^{17}$N | $^{18}$N | $^{19}$N |
|---|---|---|---|---|---|---|---|
| OWB44: | GGA | GTC | TGT | GGA | AAC | AAT | AAC |
| | GGA | GTC | TGT | ATG | AAC | AAT | AAC |
| | G | V | C | M | N | N | N |

| | $^{13}$G | $^{14}$V | | | | | |
|---|---|---|---|---|---|---|---|
| OWB45: | GGA | GTC | | | | | GC |
| | GGA | GTC | | | | | GC |
| | G | V | | | | | |

| FIG. 5A |
|---|
| FIG. 5B |

| | 35S | 36C | 37Q | 38Y | 39V | 40F | | 41P | 42A | 43H | 44K | |
|---|---|---|---|---|---|---|---|---|---|---|---|---|
| OWB77: | TCT | TGC | AAC | TAT | GTC | TTC | CC | CCA | GCT | CAC | AAG | TG |
| | TCT | TGC | AAC | GGT | GTC | TTC | CC | CCA | GCT | CAC | AAG | TG |
| | S | C | Q | G | V | F | | P | A | H | K | |

| | 36C | 37Q | 38Y | 39V | 40F | 41P | 42A | 43H | 44K | 45C | 46I | |
|---|---|---|---|---|---|---|---|---|---|---|---|---|
| OWB47: | TGC | AAC | TAT | GTC | TTC | CCA | GCT | CAC | AAG | TGT | ATC | TG |
| | TGC | AAC | TAT | GTC | ATG | CCA | GCT | CAC | AAG | TGT | ATC | TG |
| | C | Q | Y | V | M | P | A | H | K | C | I | |

| | 37Q | 38Y | 39V | 40F | 41P | 42A | 43H | 44K | 45C | 46I | |
|---|---|---|---|---|---|---|---|---|---|---|---|
| OWB48: | AAC | TAT | GTC | TTC | CCA | GCT | CAC | AAG | TGT | ATC | |
| | AAC | TAT | GTC | TTC | --- | GCT | CAC | CAA | TGT | ATC | |
| | Q | Y | V | F | - | A | H | Q | C | I | |

| | 40F | 41P | 42A | 43H | 44K | 45C | 46I | 47C | 48Y | 49F | 50C |
|---|---|---|---|---|---|---|---|---|---|---|---|
| OWB49: | TTC | CCA | GCT | CAC | AAG | TGT | ATC | TGC | TAC | TTT | CCT |
| | TTC | CCA | GCT | CAC | AAG | TGT | ATC | TGC | TAC | TTT | CCT |
| | F | P | A | H | K | C | I | C | Y | F | C |

| | 45C | 46I | 47C | 48Y | 49F | 50C |
|---|---|---|---|---|---|---|
| OWB50: | TGT | ATC | TGC | TAC | TTT | CCT |
| | TGT | ATC | TGC | ATC | TTT | CCT |
| | C | I | C | I | F | C |

Fig. 7.
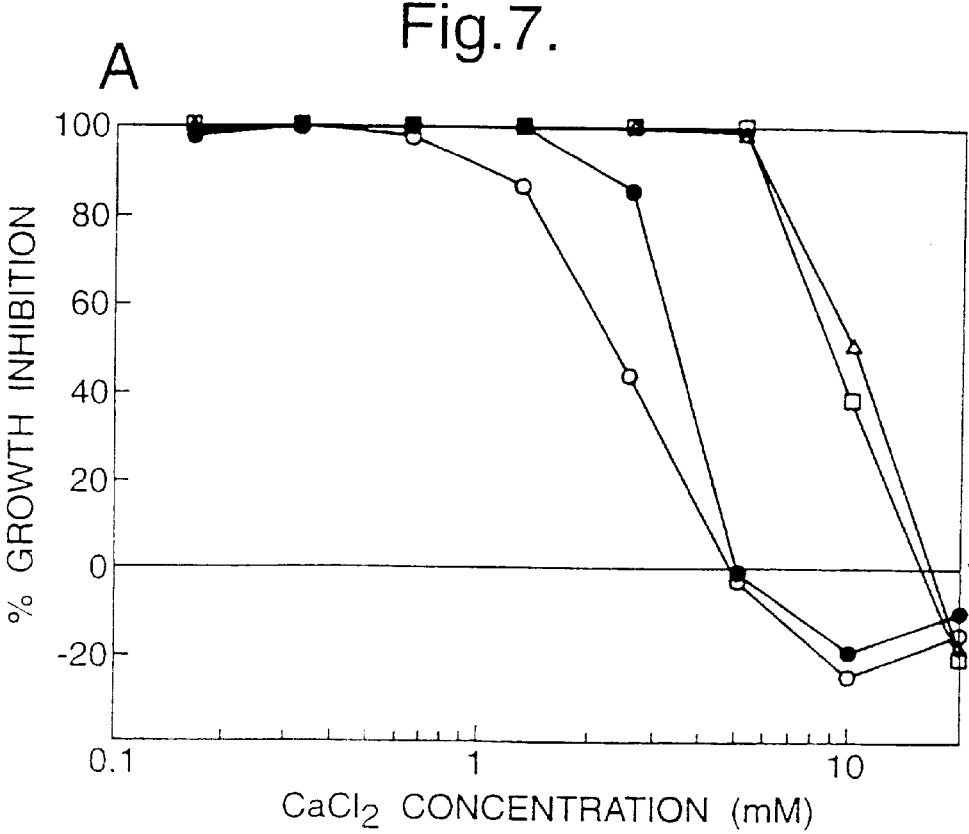
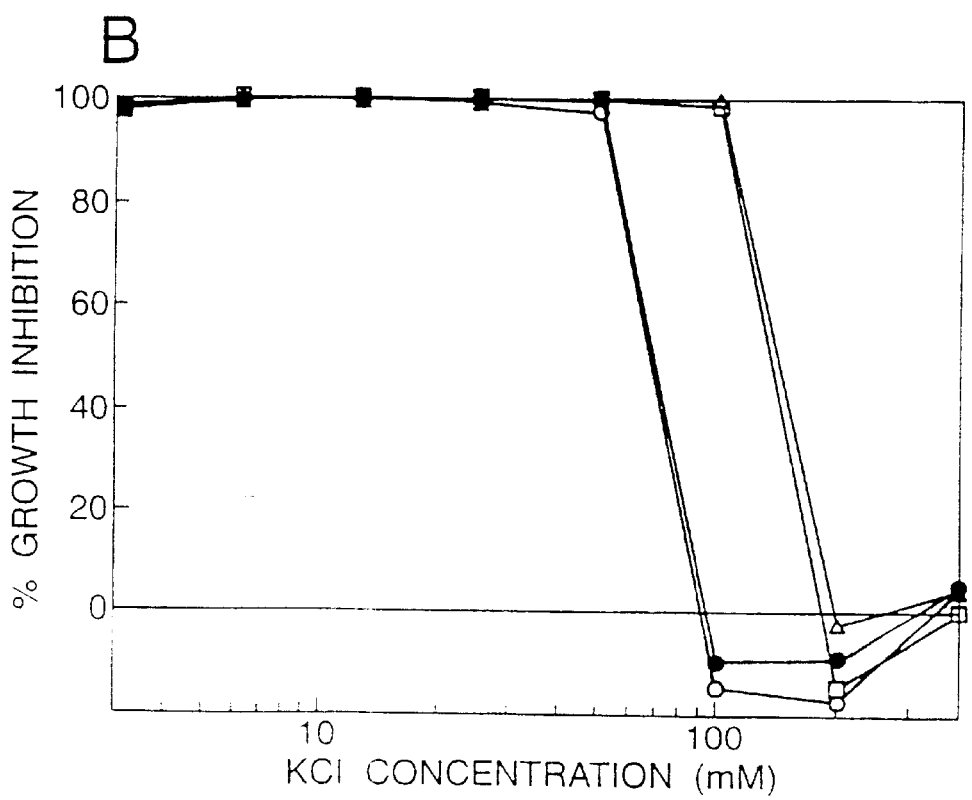

SEQUENCE LISTING

<160> NUMBER OF SEQ ID NOS: 77

<210> SEQ ID NO 1
<211> LENGTH: 36
<212> TYPE: DNA
<213> ORGANISM: Artificial Sequence
<220> FEATURE:
<223> OTHER INFORMATION: Description of Artificial Sequence:primer

<400> SEQUENCE: 1
tatcagtcga cgcatgctat tgataagatt taaagg                    36

<210> SEQ ID NO 2
<211> LENGTH: 37
<212> TYPE: DNA
<213> ORGANISM: Artificial Sequence
<220> FEATURE:
<223> OTHER INFORMATION: Description of Artificial Sequence:primer

<400> SEQUENCE: 2
aataagcttg gacaagagac agaagttgtg ccaaagg                   37

<210> SEQ ID NO 3
<211> LENGTH: 28
<212> TYPE: DNA

```
<213> ORGANISM: Artificial Sequence
<220> FEATURE:
<223> OTHER INFORMATION: Description of Artificial Sequence:primer

<400> SEQUENCE: 3
aaggatccct attaacaagg aaagtagc                                           28

<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence:primer

<400> SEQUENCE: 4
aatgctagct cagaagttgt gccaaagg                                           28

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 5
aggaaacagc tatgaccatg                                                    20

<210> SEQ ID NO 6
<211> LENGTH: 41
<212> TYPE: DNA
<213> ORGANISM: Artificial Sequence
<220> FEATURE:
<223> OTHER INFORMATION: Description of Artificial Sequence:primer

<400> SEQUENCE: 6
ggaatagccg atggagatct aggaaaacag ctatgaccat g                            41

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence:primer

<400> SEQUENCE: 7
ggaatacccg atcgagatct agga                                               24

<210> SEQ ID NO 8
<211> LENGTH: 51
<212> TYPE: PRT
<213> ORGANISM: Raphanus sativus

<400> SEQUENCE: 8
```

Gln Lys Leu Cys Glu Arg Pro Ser Gly Thr Trp Ser Gly Val Cys Gly
 1               5                  10                  15

Asn Asn Asn Ala Cys Lys Asn Gln Cys Ile Asn Leu Glu Lys Ala Arg
            20                  25                  30

His Gly Ser Cys Asn Tyr Val Phe Pro Ala His Lys Cys Ile Cys Tyr
        35                  40                  45

Phe Pro Cys
    50

```
<210> SEQ ID NO 9
<211> LENGTH: 51
```

```
<212> TYPE: PRT
<213> ORGANISM: Raphanus sativus

<400> SEQUENCE: 9

Gln Lys Leu Cys Gln Arg Pro Ser Gly Thr Trp Ser Gly Val Cys Gly
 1               5                  10                  15

Asn Asn Asn Ala Cys Lys Asn Gln Cys Ile Arg Leu Glu Lys Ala Arg
                20                  25                  30

His Gly Ser Cys Asn Tyr Val Phe Pro Ala His Lys Cys Ile Cys Tyr
            35                  40                  45

Phe Pro Cys
        50

<210> SEQ ID NO 10
<211> LENGTH: 50
<212> TYPE: PRT
<213> ORGANISM: Raphanus sativus

<400> SEQUENCE: 10

Lys Leu Cys Glu Arg Ser Ser Gly Thr Trp Ser Gly Val Cys Gly Asn
 1               5                  10                  15

Asn Asn Ala Cys Lys Asn Gln Cys Ile Arg Leu Glu Gly Ala Gln His
                20                  25                  30

Gly Ser Cys Asn Tyr Val Phe Pro Ala His Lys Cys Ile Cys Tyr Phe
            35                  40                  45

Pro Cys
    50

<210> SEQ ID NO 11
<211> LENGTH: 51
<212> TYPE: PRT
<213> ORGANISM: Raphanus sativus

<400> SEQUENCE: 11

Gln Lys Leu Cys Glu Arg Ser Ser Gly Thr Trp Ser Gly Val Cys Gly
 1               5                  10                  15

Asn Asn Asn Ala Cys Lys Asn Gln Cys Ile Asn Leu Glu Gly Ala Arg
                20                  25                  30

His Gly Ser Cys Asn Tyr Ile Phe Pro Tyr His Arg Cys Ile Cys Tyr
            35                  40                  45

Phe Pro Cys
        50

<210> SEQ ID NO 12
<211> LENGTH: 27
<212> TYPE: PRT
<213> ORGANISM: Brassica rapa

<400> SEQUENCE: 12

Gln Lys Leu Cys Glu Arg Pro Ser Gly Thr Trp Ser Gly Val Cys Gly
 1               5                  10                  15

Asn Asn Asn Ala Cys Lys Asn Gln Cys Ile Asn
                20                  25

<210> SEQ ID NO 13
<211> LENGTH: 27
<212> TYPE: PRT
<213> ORGANISM: Brassica rapa
<220> FEATURE:
<221> NAME/KEY: SITE
<222> LOCATION: (11)
```

<223> OTHER INFORMATION: Xaa is a non-standard amino acid; thought to be
      a post-translational modification of a standard
      amino acid

<400> SEQUENCE: 13

Gln Lys Leu Cys Glu Arg Pro Ser Gly Thr Xaa Ser Gly Val Cys Gly
 1               5                  10                  15

Asn Asn Asn Ala Cys Lys Asn Gln Cys Ile Arg
            20                  25

<210> SEQ ID NO 14
<211> LENGTH: 30
<212> TYPE: PRT
<213> ORGANISM: Brassica napus

<400> SEQUENCE: 14

Gln Lys Leu Cys Glu Arg Pro Ser Gly Thr Trp Ser Gly Val Cys Gly
 1               5                  10                  15

Asn Asn Asn Ala Cys Lys Asn Gln Cys Ile Asn Leu Glu Lys
            20                  25                  30

<210> SEQ ID NO 15
<211> LENGTH: 23
<212> TYPE: PRT
<213> ORGANISM: Brassica napus

<400> SEQUENCE: 15

Gln Lys Leu Cys Glu Arg Pro Ser Gly Thr Trp Ser Gly Val Cys Gly
 1               5                  10                  15

Asn Asn Asn Ala Cys Lys Asn
            20

<210> SEQ ID NO 16
<211> LENGTH: 25
<212> TYPE: PRT
<213> ORGANISM: Sinapis alba

<400> SEQUENCE: 16

Gln Lys Leu Cys Glu Arg Pro Ser Gly Thr Trp Ser Gly Val Cys Gly
 1               5                  10                  15

Asn Asn Asn Ala Cys Lys Asn Gln Cys
            20                  25

<210> SEQ ID NO 17
<211> LENGTH: 26
<212> TYPE: PRT
<213> ORGANISM: Sinapis alba

<400> SEQUENCE: 17

Gln Lys Leu Cys Gln Arg Pro Ser Gly Thr Trp Ser Gly Val Cys Gly
 1               5                  10                  15

Asn Asn Asn Ala Cys Arg Asn Gln Cys Ile
            20                  25

<210> SEQ ID NO 18
<211> LENGTH: 27
<212> TYPE: PRT
<213> ORGANISM: Arabidopsis thaliana

<400> SEQUENCE: 18

Gln Lys Leu Cys Glu Arg Pro Ser Gly Thr Trp Ser Gly Val Cys Gly
 1               5                  10                  15

Asn Ser Asn Ala Cys Lys Asn Gln Cys Ile Asn
            20                  25

<210> SEQ ID NO 19
<211> LENGTH: 414
<212> TYPE: DNA
<213> ORGANISM: Raphanus sativus

<400> SEQUENCE: 19

```
gttttattag tgatcatggc taagtttgcg tccatcatcg cacttctttt tgctgctctt      60 gttcttttg ctgctttcga agcaccaaca atggtggaag cacagaagtt gtgcgaaagg     120
ccaagtggga catggtcagg agtctgtgga acaataacg catgcaagaa tcagtgcatt     180
aaccttgaga agcacgaca tggatcttgc aactatgtct tcccagctca caagtgtatc     240
tgctactttc cttgttaatt tatcgcaaac tctttggtga atagttttta tgtaatttac     300
acaaaataag tcagtgtcac tatccatgag tgattttaag acatgtacca gatatgttat     360
gttggttcgg ttatacaaat aaagttttat tcaccaaaaa aaaaaaaaaa aaaa            414
```

<210> SEQ ID NO 20
<211> LENGTH: 51
<212> TYPE: PRT
<213> ORGANISM: Raphanus sativus

<400> SEQUENCE: 20

Gln Lys Leu Cys Gln Arg Pro Ser Gly Thr Trp Ser Gly Val Cys Gly
 1               5                  10                  15

Asn Asn Asn Ala Cys Lys Asn Gln Cys Ile Arg Leu Glu Lys Ala Arg
            20                  25                  30

His Gly Ser Cys Asn Tyr Val Phe Pro Ala His Lys Cys Ile Cys Tyr
        35                  40                  45

Phe Pro Cys
    50

<210> SEQ ID NO 21
<211> LENGTH: 47
<212> TYPE: PRT
<213> ORGANISM: Sorghum bicolor

<400> SEQUENCE: 21

Arg Val Cys Met Lys Gly Ser Ala Gly Phe Lys Gly Leu Cys Met Arg
 1               5                  10                  15

Asp Gln Asn Cys Ala Gln Val Cys Leu Gln Glu Gly Trp Gly Gly Gly
            20                  25                  30

Asn Cys Asp Gly Val Met Arg Gln Cys Lys Cys Ile Arg Gln Cys
        35                  40                  45

<210> SEQ ID NO 22
<211> LENGTH: 51
<212> TYPE: PRT
<213> ORGANISM: Raphanus sativus

<400> SEQUENCE: 22

Gln Lys Leu Cys Met Arg Pro Ser Gly Thr Trp Ser Gly Val Cys Gly
 1               5                  10                  15

Asn Asn Asn Ala Cys Lys Asn Gln Cys Ile Arg Leu Glu Lys Ala Arg
            20                  25                  30

His Gly Ser Cys Asn Tyr Val Phe Pro Ala His Lys Cys Ile Cys Tyr
        35                  40                  45

Phe Pro Cys
    50

<210> SEQ ID NO 23
<211> LENGTH: 51
<212> TYPE: PRT
<213> ORGANISM: Raphanus sativus

<400> SEQUENCE: 23

Gln Lys Leu Cys Gln Arg Pro Ser Gly Gly Trp Ser Gly Val Cys Gly
1               5                   10                  15

Asn Asn Asn Ala Cys Lys Asn Gln Cys Ile Arg Leu Glu Lys Ala Arg
            20                  25                  30

His Gly Ser Cys Asn Tyr Val Phe Pro Ala His Lys Cys Ile Cys Tyr
        35                  40                  45

Phe Pro Cys
    50

<210> SEQ ID NO 24
<211> LENGTH: 51
<212> TYPE: PRT
<213> ORGANISM: Raphanus sativus

<400> SEQUENCE: 24

Gln Lys Leu Cys Gln Arg Pro Ser Gly Thr Ser Ser Gly Val Cys Gly
1               5                   10                  15

Asn Asn Asn Ala Cys Lys Asn Gln Cys Ile Arg Leu Glu Lys Ala Arg
            20                  25                  30

His Gly Ser Cys Asn Tyr Val Phe Pro Ala His Lys Cys Ile Cys Tyr
        35                  40                  45

Phe Pro Cys
    50

<210> SEQ ID NO 25
<211> LENGTH: 51
<212> TYPE: PRT
<213> ORGANISM: Raphanus sativus

<400> SEQUENCE: 25

Gln Lys Leu Cys Gln Arg Pro Ser Gly Thr Trp Ser Gly Val Cys Met
1               5                   10                  15

Asn Asn Asn Ala Cys Lys Asn Gln Cys Ile Arg Leu Glu Lys Ala Arg
            20                  25                  30

His Gly Ser Cys Asn Tyr Val Phe Pro Ala His Lys Cys Ile Cys Tyr
        35                  40                  45

Phe Pro Cys
    50

<210> SEQ ID NO 26
<211> LENGTH: 51
<212> TYPE: PRT
<213> ORGANISM: Raphanus sativus

<400> SEQUENCE: 26

Gln Lys Leu Cys Gln Arg Pro Ser Gly Thr Trp Ser Gly Val Cys Gly
1               5                   10                  15

Asn Asn Asn Ala Cys Lys Asn Gln Cys Ile Arg Leu Glu Lys Trp Arg
            20                  25                  30

His Gly Ser Cys Asn Tyr Val Phe Pro Ala His Lys Cys Ile Cys Tyr
        35                  40                  45

```
Phe Pro Cys
     50

<210> SEQ ID NO 27
<211> LENGTH: 51
<212> TYPE: PRT
<213> ORGANISM: Raphanus sativus

<400> SEQUENCE: 27

Gln Lys Leu Cys Gln Arg Pro Ser Gly Thr Trp Ser Gly Val Cys Gly
 1               5                  10                  15

Asn Asn Asn Ala Cys Lys Asn Gln Cys Ile Arg Leu Glu Lys Ala Arg
            20                  25                  30

His Gly Ser Cys Asn Gly Val Phe Pro Ala His Lys Cys Ile Cys Tyr
        35                  40                  45

Phe Pro Cys
     50

<210> SEQ ID NO 28
<211> LENGTH: 51
<212> TYPE: PRT
<213> ORGANISM: Raphanus sativus

<400> SEQUENCE: 28

Gln Lys Leu Cys Gln Arg Pro Ser Gly Thr Trp Ser Gly Val Cys Gly
 1               5                  10                  15

Asn Asn Asn Ala Cys Lys Asn Gln Cys Ile Arg Leu Glu Lys Ala Arg
            20                  25                  30

His Gly Ser Cys Asn Tyr Val Met Pro Ala His Lys Cys Ile Cys Tyr
        35                  40                  45

Phe Pro Cys
     50

<210> SEQ ID NO 29
<211> LENGTH: 51
<212> TYPE: PRT
<213> ORGANISM: Raphanus sativus

<400> SEQUENCE: 29

Gln Lys Leu Cys Gln Arg Pro Ser Gly Thr Trp Ser Gly Val Cys Gly
 1               5                  10                  15

Asn Asn Asn Ala Cys Lys Asn Gln Cys Ile Arg Leu Glu Lys Ala Arg
            20                  25                  30

His Gly Ser Cys Asn Tyr Val Phe Pro Ala His Gln Cys Ile Cys Tyr
        35                  40                  45

Phe Pro Cys
     50

<210> SEQ ID NO 30
<211> LENGTH: 51
<212> TYPE: PRT
<213> ORGANISM: Raphanus sativus

<400> SEQUENCE: 30

Gln Lys Leu Cys Gln Arg Pro Ser Gly Thr Trp Ser Gly Val Cys Gly
 1               5                  10                  15

Asn Asn Asn Ala Cys Lys Asn Gln Cys Ile Arg Leu Glu Lys Ala Arg
            20                  25                  30

His Gly Ser Cys Asn Tyr Val Pro Pro Ala His Lys Cys Ile Cys Ile
```

35                  40                  45

Phe Pro Cys
    50

<210> SEQ ID NO 31
<211> LENGTH: 51
<212> TYPE: PRT
<213> ORGANISM: Raphanus sativus

<400> SEQUENCE: 31

Gln Lys Leu Cys Gln Arg Pro Ser Gly Ala Trp Ser Gly Val Cys Gly
 1               5                  10                  15

Asn Asn Asn Ala Cys Lys Asn Gln Cys Ile Arg Leu Glu Lys Ala Arg
                20                  25                  30

His Gly Ser Cys Asn Tyr Val Phe Pro Ala His Lys Cys Ile Cys Tyr
            35                  40                  45

Phe Pro Cys
    50

<210> SEQ ID NO 32
<211> LENGTH: 51
<212> TYPE: PRT
<213> ORGANISM: Raphanus sativus

<400> SEQUENCE: 32

Gln Lys Leu Cys Gln Arg Pro Ser Gly Thr Trp Ser Gly Val Cys Gly
 1               5                  10                  15

Asn Asn Asn Ala Cys Lys Asn Gln Cys Ile Arg Leu Glu Lys Ala Arg
                20                  25                  30

Ala Gly Ser Cys Asn Tyr Val Phe Pro Ala His Lys Cys Ile Cys Tyr
            35                  40                  45

Phe Pro Cys
    50

<210> SEQ ID NO 33
<211> LENGTH: 51
<212> TYPE: PRT
<213> ORGANISM: Raphanus sativus

<400> SEQUENCE: 33

Gln Lys Leu Cys Gln Arg Pro Ser Gly Thr Trp Ser Gly Val Cys Gly
 1               5                  10                  15

Asn Asn Asn Ala Cys Lys Asn Gln Cys Ile Arg Leu Glu Lys Ala Arg
                20                  25                  30

His Gly Ser Cys Asn Ala Val Phe Pro Ala His Lys Cys Ile Cys Tyr
            35                  40                  45

Phe Pro Cys
    50

<210> SEQ ID NO 34
<211> LENGTH: 51
<212> TYPE: PRT
<213> ORGANISM: Raphanus sativus

<400> SEQUENCE: 34

Gln Lys Leu Cys Gln Arg Pro Ser Gly Thr Trp Ser Gly Val Cys Gly
 1               5                  10                  15

Asn Asn Asn Ala Cys Lys Asn Gln Cys Ile Arg Leu Glu Lys Ala Arg
                20                  25                  30

His Gly Ser Cys Asn Tyr Val Ala Pro Ala His Lys Cys Ile Cys Tyr
            35                  40                  45

Phe Pro Cys
        50

<210> SEQ ID NO 35
<211> LENGTH: 50
<212> TYPE: PRT
<213> ORGANISM: Raphanus sativus

<400> SEQUENCE: 35

Gln Lys Leu Cys Gln Arg Ser Gly Thr Trp Ser Gly Val Cys Gly Asn
  1               5                  10                  15

Asn Asn Ala Cys Lys Asn Gln Cys Ile Arg Leu Glu Lys Ala Arg His
             20                  25                  30

Gly Ser Cys Asn Tyr Val Phe Pro Ala His Lys Cys Ile Cys Tyr Phe
            35                  40                  45

Pro Cys
    50

<210> SEQ ID NO 36
<211> LENGTH: 50
<212> TYPE: PRT
<213> ORGANISM: Raphanus sativus

<400> SEQUENCE: 36

Gln Lys Leu Cys Gln Arg Pro Ser Gly Thr Trp Ser Gly Val Cys Gly
  1               5                  10                  15

Asn Asn Asn Ala Cys Lys Asn Gln Cys Ile Arg Leu Glu Lys Ala Arg
             20                  25                  30

His Gly Ser Cys Asn Tyr Val Pro Ala His Lys Cys Ile Cys Tyr Phe
            35                  40                  45

Pro Cys
    50

<210> SEQ ID NO 37
<211> LENGTH: 51
<212> TYPE: PRT
<213> ORGANISM: Raphanus sativus

<400> SEQUENCE: 37

Gln Lys Leu Cys Gln Arg Arg Ser Gly Thr Trp Ser Gly Val Cys Gly
  1               5                  10                  15

Asn Asn Asn Ala Cys Lys Asn Gln Cys Ile Arg Leu Glu Lys Ala Arg
             20                  25                  30

His Gly Ser Cys Asn Tyr Val Phe Pro Ala His Lys Cys Ile Cys Tyr
            35                  40                  45

Phe Pro Cys
        50

<210> SEQ ID NO 38
<211> LENGTH: 51
<212> TYPE: PRT
<213> ORGANISM: Raphanus sativus

<400> SEQUENCE: 38

Gln Lys Leu Cys Gln Arg Pro Ser Arg Thr Trp Ser Gly Val Cys Gly
  1               5                  10                  15

Asn Asn Asn Ala Cys Lys Asn Gln Cys Ile Arg Leu Glu Lys Ala Arg
             20                  25                  30

His Gly Ser Cys Asn Tyr Val Phe Pro Ala His Lys Cys Ile Cys Tyr
            35                  40                  45

Phe Pro Cys
        50

<210> SEQ ID NO 39
<211> LENGTH: 51
<212> TYPE: PRT
<213> ORGANISM: Raphanus sativus

<400> SEQUENCE: 39

Gln Lys Leu Cys Gln Arg Pro Ser Gly Thr Trp Arg Gly Val Cys Gly
 1               5                  10                  15

Asn Asn Asn Ala Cys Lys Asn Gln Cys Ile Arg Leu Glu Lys Ala Arg
            20                  25                  30

His Gly Ser Cys Asn Tyr Val Phe Pro Ala His Lys Cys Ile Cys Tyr
            35                  40                  45

Phe Pro Cys
        50

<210> SEQ ID NO 40
<211> LENGTH: 51
<212> TYPE: PRT
<213> ORGANISM: Raphanus sativus

<400> SEQUENCE: 40

Gln Lys Leu Cys Gln Arg Pro Ser Gly Thr Trp Ser Gly Val Cys Gly
 1               5                  10                  15

Asn Asn Asn Ala Cys Lys Asn Gln Cys Arg Arg Leu Glu Lys Ala Arg
            20                  25                  30

His Gly Ser Cys Asn Tyr Val Phe Pro Ala His Lys Cys Ile Cys Tyr
            35                  40                  45

Phe Pro Cys
        50

<210> SEQ ID NO 41
<211> LENGTH: 51
<212> TYPE: PRT
<213> ORGANISM: Raphanus sativus

<400> SEQUENCE: 41

Gln Lys Leu Cys Gln Arg Pro Ser Gly Thr Trp Ser Gly Val Cys Gly
 1               5                  10                  15

Asn Asn Asn Ala Cys Lys Asn Gln Cys Ile Arg Arg Glu Lys Ala Arg
            20                  25                  30

His Gly Ser Cys Asn Tyr Val Phe Pro Ala His Lys Cys Ile Cys Tyr
            35                  40                  45

Phe Pro Cys
        50

<210> SEQ ID NO 42
<211> LENGTH: 51
<212> TYPE: PRT
<213> ORGANISM: Raphanus sativus

<400> SEQUENCE: 42

Gln Lys Leu Cys Gln Arg Pro Ser Gly Thr Trp Ser Gly Val Cys Gly
 1               5                  10                  15

Asn Asn Asn Ala Cys Lys Asn Gln Cys Ile Arg Leu Glu Lys Ala Arg

```
                   20                  25                  30

His Gly Ser Cys Arg Tyr Val Phe Pro Ala His Lys Cys Ile Cys Tyr
            35                  40                  45

Phe Pro Cys
        50

<210> SEQ ID NO 43
<211> LENGTH: 51
<212> TYPE: PRT
<213> ORGANISM: Raphanus sativus

<400> SEQUENCE: 43

Gln Lys Leu Cys Gln Arg Pro Ser Gly Thr Trp Ser Gly Val Cys Gly
 1               5                  10                  15

Asn Asn Asn Ala Cys Lys Asn Gln Cys Ile Arg Leu Glu Lys Ala Arg
                20                  25                  30

His Gly Ser Cys Asn Tyr Arg Phe Pro Ala His Lys Cys Ile Cys Tyr
            35                  40                  45

Phe Pro Cys
        50

<210> SEQ ID NO 44
<211> LENGTH: 51
<212> TYPE: PRT
<213> ORGANISM: Raphanus sativus

<400> SEQUENCE: 44

Gln Lys Leu Cys Gln Arg Pro Ser Gly Thr Trp Ser Gly Val Cys Gly
 1               5                  10                  15

Asn Asn Asn Ala Cys Lys Asn Gln Cys Ile Arg Leu Glu Lys Ala Arg
                20                  25                  30

His Gly Ser Cys Asn Tyr Val Phe Pro Arg His Lys Cys Ile Cys Tyr
            35                  40                  45

Phe Pro Cys
        50

<210> SEQ ID NO 45
<211> LENGTH: 51
<212> TYPE: PRT
<213> ORGANISM: Raphanus sativus

<400> SEQUENCE: 45

Gln Lys Leu Cys Gln Arg Pro Ser Gly Thr Trp Ser Gly Val Cys Gly
 1               5                  10                  15

Asn Asn Asn Ala Cys Lys Asn Gln Cys Ile Arg Leu Glu Lys Ala Arg
                20                  25                  30

His Gly Ser Cys Asn Tyr Val Phe Pro Ala His Lys Cys Arg Cys Tyr
            35                  40                  45

Phe Pro Cys
        50

<210> SEQ ID NO 46
<211> LENGTH: 51
<212> TYPE: PRT
<213> ORGANISM: Raphanus sativus

<400> SEQUENCE: 46

Gln Lys Leu Cys Gln Arg Pro Ser Gly Thr Trp Ser Gly Val Cys Gly
 1               5                  10                  15
```

```
Asn Asn Asn Ala Cys Lys Asn Gln Cys Ile Arg Leu Glu Lys Ala Arg
             20                  25                  30

His Gly Ser Cys Asn Tyr Val Phe Pro Ala His Lys Cys Ile Cys Tyr
         35                  40                  45

Arg Pro Cys
     50
```

<210> SEQ ID NO 47
<211> LENGTH: 43
<212> TYPE: DNA
<213> ORGANISM: Artificial Sequence
<220> FEATURE:
<223> OTHER INFORMATION: Description of Artificial Sequence:primer

<400> SEQUENCE: 47
aataagcttt ggacaagaga cagaagttgt gcatgaggcc aag              43

<210> SEQ ID NO 48
<211> LENGTH: 27
<212> TYPE: DNA
<213> ORGANISM: Artificial Sequence
<220> FEATURE:
<223> OTHER INFORMATION: Description of Artificial Sequence:primer

<400> SEQUENCE: 48
ttgtgccaaa ggnnnagtgg gacatgg                                27

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 49
ccaagtgggg gttggtcagg                                        20

<210> SEQ ID NO 50
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 50
agtgggacat cctcaggagt c                                      21

<210> SEQ ID NO 51
<211> LENGTH: 23
<212> TYPE: DNA
<213> ORGANISM: Artificial Sequence
<220> FEATURE:
<223> OTHER INFORMATION: Description of Artificial Sequence:primer

<400> SEQUENCE: 51
ggagtctgta tgaacaataa cgc                                    23

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 52

-continued

```
tcttgcaacg gtgtcttccc                                          20

<210> SEQ ID NO 53
<211> LENGTH: 22
<212> TYPE: DNA
<213> ORGANISM: Artificial Sequence
<220> FEATURE:
<223> OTHER INFORMATION: Description of Artificial Sequence:primer

<400> SEQUENCE: 53
tgcaactatg tcatgccagc ta                                       22

<210> SEQ ID NO 54
<211> LENGTH: 23
<212> TYPE: DNA
<213> ORGANISM: Artificial Sequence
<220> FEATURE:
<223> OTHER INFORMATION: Description of Artificial Sequence:primer

<400> SEQUENCE: 54
ttcccagctc accaatgtat ctg                                      23

<210> SEQ ID NO 55
<211> LENGTH: 26
<212> TYPE: DNA
<213> ORGANISM: Artificial Sequence
<220> FEATURE:
<223> OTHER INFORMATION: Description of Artificial Sequence:primer

<400> SEQUENCE: 55
aactatgtct tcnnngctca caagtg                                   26

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 56
tgtatctgca tctttccttg                                          20

<210> SEQ ID NO 57
<211> LENGTH: 51
<212> TYPE: PRT
<213> ORGANISM: Raphanus sativus

<400> SEQUENCE: 57

Gln Lys Leu Cys Glu Arg Pro Ser Arg Thr Trp Ser Gly Val Cys Gly
  1               5                  10                  15

Asn Asn Asn Ala Cys Lys Asn Gln Cys Ile Asn Leu Glu Lys Ala Arg
             20                  25                  30

His Gly Ser Cys Asn Tyr Val Phe Pro Ala His Lys Cys Ile Cys Tyr
         35                  40                  45

Phe Pro Cys
     50

<210> SEQ ID NO 58
<211> LENGTH: 51
<212> TYPE: PRT
<213> ORGANISM: Raphanus sativus

<400> SEQUENCE: 58

Gln Lys Leu Cys Glu Arg Pro Ser Gly Thr Trp Ser Gly Val Cys Gly
```

```
                    1               5              10              15
          Asn Asn Asn Ala Cys Lys Asn Gln Cys Ile Asn Leu Glu Lys Ala Arg
                          20                  25                  30

His Gly Ser Cys Asn Tyr Arg Phe Pro Ala His Lys Cys Ile Cys Tyr
                      35                  40                  45

Phe Pro Cys
                  50

<210> SEQ ID NO 59
<211> LENGTH: 51
<212> TYPE: PRT
<213> ORGANISM: Raphanus sativus

<400> SEQUENCE: 59

Gln Lys Leu Cys Glu Arg Pro Ser Arg Thr Trp Ser Gly Val Cys Gly
            1               5                  10                  15

Asn Asn Asn Ala Cys Lys Asn Gln Cys Ile Asn Leu Glu Lys Ala Arg
                          20                  25                  30

His Gly Ser Cys Asn Tyr Arg Phe Pro Ala His Lys Cys Ile Cys Tyr
                      35                  40                  45

Phe Pro Cys
                  50

<210> SEQ ID NO 60
<211> LENGTH: 51
<212> TYPE: PRT
<213> ORGANISM: Raphanus sativus

<400> SEQUENCE: 60

Gln Lys Leu Cys Met Arg Pro Ser Gly Thr Trp Ser Gly Val Cys Gly
            1               5                  10                  15

Asn Asn Asn Ala Cys Lys Asn Gln Cys Ile Asn Leu Glu Lys Ala Arg
                          20                  25                  30

His Gly Ser Cys Asn Tyr Val Phe Pro Ala His Lys Cys Ile Cys Tyr
                      35                  40                  45

Phe Pro Cys
                  50

<210> SEQ ID NO 61
<211> LENGTH: 51
<212> TYPE: PRT
<213> ORGANISM: Raphanus sativus

<400> SEQUENCE: 61

Gln Lys Leu Cys Glu Arg Pro Ser Gly Thr Trp Ser Gly Val Cys Met
            1               5                  10                  15

Asn Asn Asn Ala Cys Lys Asn Gln Cys Ile Asn Leu Glu Lys Ala Arg
                          20                  25                  30

His Gly Ser Cys Asn Tyr Val Phe Pro Ala His Lys Cys Ile Cys Tyr
                      35                  40                  45

Phe Pro Cys
                  50

<210> SEQ ID NO 62
<211> LENGTH: 51
<212> TYPE: PRT
<213> ORGANISM: Raphanus sativus

<400> SEQUENCE: 62
```

-continued

Gln Lys Leu Cys Gln Arg Pro Ser Arg Thr Trp Ser Gly Val Cys Gly
 1               5                  10                  15

Asn Asn Asn Ala Cys Lys Asn Gln Cys Ile Arg Leu Glu Lys Ala Arg
                20                  25                  30

His Gly Ser Cys Asn Tyr Val Phe Pro Ala His Lys Cys Ile Cys Tyr
            35                  40                  45

Phe Pro Cys
        50

<210> SEQ ID NO 63
<211> LENGTH: 51
<212> TYPE: PRT
<213> ORGANISM: Raphanus sativus

<400> SEQUENCE: 63

Gln Lys Leu Cys Gln Arg Pro Ser Gly Thr Trp Ser Gly Val Cys Gly
 1               5                  10                  15

Asn Asn Asn Ala Cys Lys Asn Gln Cys Ile Arg Leu Glu Lys Ala Arg
                20                  25                  30

His Gly Ser Cys Asn Tyr Arg Phe Pro Ala His Lys Cys Ile Cys Tyr
            35                  40                  45

Phe Pro Cys
        50

<210> SEQ ID NO 64
<211> LENGTH: 51
<212> TYPE: PRT
<213> ORGANISM: Raphanus sativus

<400> SEQUENCE: 64

Gln Lys Leu Cys Gln Arg Pro Ser Arg Thr Trp Ser Gly Val Cys Gly
 1               5                  10                  15

Asn Asn Asn Ala Cys Lys Asn Gln Cys Ile Arg Leu Glu Lys Ala Arg
                20                  25                  30

His Gly Ser Cys Asn Tyr Arg Phe Pro Ala His Lys Cys Ile Cys Tyr
            35                  40                  45

Phe Pro Cys
        50

<210> SEQ ID NO 65
<211> LENGTH: 51
<212> TYPE: PRT
<213> ORGANISM: Raphanus sativus

<400> SEQUENCE: 65

Gln Lys Leu Cys Met Arg Pro Ser Gly Thr Trp Ser Gly Val Cys Gly
 1               5                  10                  15

Asn Asn Asn Ala Cys Lys Asn Gln Cys Ile Arg Leu Glu Lys Ala Arg
                20                  25                  30

His Gly Ser Cys Asn Tyr Val Phe Pro Ala His Lys Cys Ile Cys Tyr
            35                  40                  45

Phe Pro Cys
        50

<210> SEQ ID NO 66
<211> LENGTH: 51
<212> TYPE: PRT
<213> ORGANISM: Raphanus sativus

<400> SEQUENCE: 66

Gln Lys Leu Cys Gln Arg Pro Ser Gly Thr Trp Ser Gly Val Cys Met
1               5                   10                  15

Asn Asn Asn Ala Cys Lys Asn Gln Cys Ile Arg Leu Glu Lys Ala Arg
                20                  25                  30

His Gly Ser Cys Asn Tyr Val Phe Pro Ala His Lys Cys Ile Cys Tyr
            35                  40                  45

Phe Pro Cys
        50

<210> SEQ ID NO 67
<211> LENGTH: 50
<212> TYPE: PRT
<213> ORGANISM: Raphanus sativus

<400> SEQUENCE: 67

Lys Leu Cys Glu Arg Ser Ser Arg Thr Trp Ser Gly Val Cys Gly Asn
1               5                   10                  15

Asn Asn Ala Cys Lys Asn Gln Cys Ile Arg Leu Glu Gly Ala Gln His
                20                  25                  30

Gly Ser Cys Asn Tyr Val Phe Pro Ala His Lys Cys Ile Cys Tyr Phe
            35                  40                  45

Pro Cys
    50

<210> SEQ ID NO 68
<211> LENGTH: 50
<212> TYPE: PRT
<213> ORGANISM: Raphanus sativus

<400> SEQUENCE: 68

Lys Leu Cys Glu Arg Ser Ser Gly Thr Trp Ser Gly Val Cys Gly Asn
1               5                   10                  15

Asn Asn Ala Cys Lys Asn Gln Cys Ile Arg Leu Glu Gly Ala Gln His
                20                  25                  30

Gly Ser Cys Asn Tyr Arg Phe Pro Ala His Lys Cys Ile Cys Tyr Phe
            35                  40                  45

Pro Cys
    50

<210> SEQ ID NO 69
<211> LENGTH: 50
<212> TYPE: PRT
<213> ORGANISM: Raphanus sativus

<400> SEQUENCE: 69

Lys Leu Cys Glu Arg Ser Ser Arg Thr Trp Ser Gly Val Cys Gly Asn
1               5                   10                  15

Asn Asn Ala Cys Lys Asn Gln Cys Ile Arg Leu Glu Gly Ala Gln His
                20                  25                  30

Gly Ser Cys Asn Tyr Arg Phe Pro Ala His Lys Cys Ile Cys Tyr Phe
            35                  40                  45

Pro Cys
    50

<210> SEQ ID NO 70
<211> LENGTH: 50
<212> TYPE: PRT
<213> ORGANISM: Raphanus sativus -continued

```
<400> SEQUENCE: 70

Lys Leu Cys Met Arg Ser Ser Gly Thr Trp Ser Gly Val Cys Gly Asn
 1               5                  10                  15

Asn Asn Ala Cys Lys Asn Gln Cys Ile Arg Leu Glu Gly Ala Gln His
            20                  25                  30

Gly Ser Cys Asn Tyr Val Phe Pro Ala His Lys Cys Ile Cys Tyr Phe
        35                  40                  45

Pro Cys
    50

<210> SEQ ID NO 71
<211> LENGTH: 50
<212> TYPE: PRT
<213> ORGANISM: Raphanus sativus

<400> SEQUENCE: 71

Lys Leu Cys Glu Arg Ser Ser Gly Thr Trp Ser Gly Val Cys Met Asn
 1               5                  10                  15

Asn Asn Ala Cys Lys Asn Gln Cys Ile Arg Leu Glu Gly Ala Gln His
            20                  25                  30

Gly Ser Cys Asn Tyr Val Phe Pro Ala His Lys Cys Ile Cys Tyr Phe
        35                  40                  45

Pro Cys
    50

<210> SEQ ID NO 72
<211> LENGTH: 51
<212> TYPE: PRT
<213> ORGANISM: Raphanus sativus

<400> SEQUENCE: 72

Gln Lys Leu Cys Glu Arg Ser Ser Arg Thr Trp Ser Gly Val Cys Gly
 1               5                  10                  15

Asn Asn Asn Ala Cys Lys Asn Gln Cys Ile Asn Leu Glu Gly Ala Arg
            20                  25                  30

His Gly Ser Cys Asn Tyr Ile Phe Pro Tyr His Arg Cys Ile Cys Tyr
        35                  40                  45

Phe Pro Cys
    50

<210> SEQ ID NO 73
<211> LENGTH: 51
<212> TYPE: PRT
<213> ORGANISM: Raphanus sativus

<400> SEQUENCE: 73

Gln Lys Leu Cys Glu Arg Ser Ser Gly Thr Trp Ser Gly Val Cys Gly
 1               5                  10                  15

Asn Asn Asn Ala Cys Lys Asn Gln Cys Ile Asn Leu Glu Gly Ala Arg
            20                  25                  30

His Gly Ser Cys Asn Tyr Arg Phe Pro Tyr His Arg Cys Ile Cys Tyr
        35                  40                  45

Phe Pro Cys
    50

<210> SEQ ID NO 74
<211> LENGTH: 51
<212> TYPE: PRT
<213> ORGANISM: Raphanus sativus
```

-continued

```
<400> SEQUENCE: 74

Gln Lys Leu Cys Glu Arg Ser Ser Arg Thr Trp Ser Gly Val Cys Gly
  1               5                  10                  15

Asn Asn Asn Ala Cys Lys Asn Gln Cys Ile Asn Leu Glu Gly Ala Arg
             20                  25                  30

His Gly Ser Cys Asn Tyr Arg Phe Pro Tyr His Arg Cys Ile Cys Tyr
         35                  40                  45

Phe Pro Cys
     50

<210> SEQ ID NO 75
<211> LENGTH: 51
<212> TYPE: PRT
<213> ORGANISM: Raphanus sativus

<400> SEQUENCE: 75

Gln Lys Leu Cys Met Arg Ser Ser Gly Thr Trp Ser Gly Val Cys Gly
  1               5                  10                  15

Asn Asn Asn Ala Cys Lys Asn Gln Cys Ile Asn Leu Glu Gly Ala Arg
             20                  25                  30

His Gly Ser Cys Asn Tyr Ile Phe Pro Tyr His Arg Cys Ile Cys Tyr
         35                  40                  45

Phe Pro Cys
     50

<210> SEQ ID NO 76
<211> LENGTH: 51
<212> TYPE: PRT
<213> ORGANISM: Raphanus sativus

<400> SEQUENCE: 76

Gln Lys Leu Cys Glu Arg Ser Ser Gly Thr Trp Ser Gly Val Cys Met
  1               5                  10                  15

Asn Asn Asn Ala Cys Lys Asn Gln Cys Ile Asn Leu Glu Gly Ala Arg
             20                  25                  30

His Gly Ser Cys Asn Tyr Ile Phe Pro Tyr His Arg Cys Ile Cys Tyr
         35                  40                  45

Phe Pro Cys
     50

<210> SEQ ID NO 77
<211> LENGTH: 51
<212> TYPE: PRT
<213> ORGANISM: Raphanus sativus
<220> FEATURE:
<221> NAME/KEY: SITE
<222> LOCATION: (1)
<223> OTHER INFORMATION: Xaa is pyroglutamyl

<400> SEQUENCE: 77

Xaa Lys Leu Cys Gln Arg Pro Ser Gly Thr Trp Ser Gly Val Cys Gly
  1               5                  10                  15

Asn Asn Asn Ala Cys Lys Asn Gln Cys Ile Arg Leu Glu Lys Ala Arg
             20                  25                  30

His Gly Ser Cys Asn Tyr Val Phe Pro Ala His Lys Cys Ile Cys Tyr
         35                  40                  45

Phe Pro Cys
     50
```

ANTIFUNGAL PROTEINS

FIELD OF INVENTION

This invention relates to antifungal proteins, processes for their manufacture and use, and DNA sequences encoding them.

In this context, antifungal proteins are defined as proteins or peptides possessing antifungal activity. Activity includes a range of antagonistic effects such as partial inhibition or death.

BACKGROUND

A wide range of antifungal proteins with activity against plant pathogenic fungi have been isolated from certain plant species. We have previously described a class of antifungal proteins capable of isolation from radish and other plant species. These proteins are described in the following publications which are specifically incorporated herein by reference: International Patent Application Publication Number WO93/05153 published Mar. 18, 1993; Terras FRG et al, 1992, J Biol Chem, 267:15301–15309; Terras et al, FEBS Lett, 1993, 316:233–240; Terras et al, 1995, Plant Cell, 7:573–588. The class includes Rs-AFP1 (antifungal protein 1), Rs-AFP2, Rs-AFP3 and Rs-AFP4 from *Raphanus sativus* and homologous proteins such as Bn-AFP1 and Bn-AFP2 from *Brassica napus,* Br-AFP1 and Br-AFP2 from *Brassica rapa,* Sa-AFP1 and Sa-AFP2 from *Sinapis alba,* At-AFP1 from *Arabidopsis thaliana,* Dm-AMP1 and Dm-AMP2 from *Dahlia merckii,* Cb-AMP1 and Cb-AMP2 from *Cnicus benedictus,* Lc-AFP from *Lathyrus cicera,* Ct-AMP1 and Ct-AMP2 from *Clitoria ternatea.* The proteins specifically inhibit a range of fungi and may be used as fungicides for agricultural or pharmaceutical or preservative purposes. It has been proposed that this class of antifungal proteins should be named as plant defensins (Terras F. R. G. et al 1995, Plant Cell 7 573–588) and these proteins share a similar motif of conserved cysteines and glycines (Broekaert et al 1995 Plant Physiol 108 1353–1358).

FIG. 1 shows the amino acid sequences of the protein Rs-AFP2 (SEQ ID NO: 9) and the substantially homologous proteins Rs-AFP1 (SEQ ID NO: 8), Rs-AFP3 (SEQ ID NO: 10), Rs-AFP4 (SEQ ID NO: 11), Br-AFP1 (SEQ ID NO: 12), Br-AFP2 (SEQ ID NO: 13), Bn-AFP1 (SEQ ID NO: 14), Bn-AFP2 (SEQ ID NO: 15), Sa-AFP1 (SEQ ID NO: 16), Sa-AFP2 (SEQ ID NO: 17) and At-AFP1 (SEQ ID NO: 18) which are small 5 kDa polypeptides that are highly basic and rich in cysteine. FIG. 1 numbers the positions of the amino acid residues: the dash (-) at the start of the Rs-AFP3 sequence indicates a gap introduced for maximum alignment. The sequences shown for Br-AFP1, Br-AFP2, Bn-AFP1, Bn-AFP2, Sa-AFP1, Sa-AFP2 and At-AFP1 are not complete: only the N-terminal sequences are shown. The question mark (?) in the Br-AFP2 sequence indicates a non-standard amino acid which the sequencing could not assign and which is thought to be a post-translational modification on one of the standard amino acid residues.

The primary structures of the two antifungal protein isoforms capable of isolation from radish seeds, Rs-AFP1 (SEQ ID NO: 8) and Rs-AFP2 (SEQ ID NO: 9), only differ at two positions: the glutamic acid residue (E) at position 5 in Rs-AFP1 (SEQ ID NO: 8) is a glutamine residue (Q) in Rs-AFP2 (SEQ ID NO: 9), and the asparagine residue (N) at position 27 in Rs-AFP1 (SEQ ID NO: 8) is substituted by an arginine residue (R) in Rs-AFP2 (SEQ ID NO: 9). As a result, Rs-AFP2 (SEQ ID NO: 9) has a higher net positive charge (+2) at physiological pH. Although both Rs-AFPs are 94% identical at the amino acid sequence level, Rs-AFP2 (SEQ ID NO: 9) is two- to thirty-fold more active than Rs-AFP1 (SEQ ID NO: 8) on various fungi and shows an increased salt-tolerence. The proteins Rs-AFP3 (SEQ ID NO: 10) and Rs-AFP4 (SEQ ID NO: 11) are found in radish leaves following localized fungal infection. The induced leaf proteins are homologous to Rs-AFP1 (SEQ ID NO: 8) and Rs-AFP2 (SEQ ID NO: 9) and exert similar antifungal activity in vitro.

The cDNA encoding Rs-AFP1 (SEQ ID NO: 19) encodes a preprotein with a signal peptide followed by the mature protein. The cDNA sequence is shown n FIG. 2. *Saccharomyces cerevisiae* can be used as a vector for the production and secretion of Rs-AFP2 (Vilas Alves et al, FEBS Lett, 1994, 348:228–232). Plant-derivable "wild-type" Rs-AFP2 can be correctly processed and secreted by yeast when expressed as a N-terminal fusion to the yeast mating factor α1 (MFα1) preprosequence. The Rs-AFP2 protein does not have adverse effects on yeast even at concentrations as high as 500 μg/ml.

We now provide new potent antifungal proteins based on the structure of the Rs-AFPs and related proteins.

SUMMARY OF THE INVENTION

According to a first aspect the invention provides an antifungal protein having an amino acid sequence which is substantially homologous to the Rs-AFP2 sequence (SEQ ID NO: 9) shown in FIG. 1 and containing at least one mutation selected from the group consisting of a basic residue at position 9, a basic residue at position 39, a hydrophobic residue at position 5 and a hydrophobic residue at position 16.

According to a preferred embodiment of the first aspect of the present invention there is provided an antifungal protein having an amino acid sequence which is substantially homologous to the Rs-AFP2 sequence (SEQ ID NO: 9) shown in FIG. 1 and containing at least one mutation selected from the group consisting of an arginine residue at position 9, an arginine residue at position 39, a methionine residue at position 5 and a methionine residue at position 16. An antifungal protein having both a mutation to arginine at position 9 and a mutation to arginine at position 39 may be particularly active.

Proteins which are substantially homologous to the Rs-AFP2 protein include the proteins Rs-AFP1 (SEQ ID NO: 8), Rs-AFP3 (SEQ ID NO: 10), Rs-AFP4 (SEQ ID NO: 11), Br-AFP1 (SEQ ID NO: 12), Br-AFP2 (SEQ ID NO: 13), Bn-AFP1 (SEQ ID NO: 14), Bn-AFP2 (SEQ ID NO: 15), Sa-AFP1 (SEQ ID NO: 16), Sa-AFP2 (SEQ ID NO: 17) and At-AFP1 (SEQ ID NO: 18) shown in FIG. 1.

As used herein the term substantially homologous denotes those proteins which have an amino acid sequence with at least 40% identity, preferably at least 60% identity and most preferably at least 80% identity to the Rs-AFP2 sequence (SEQ ID NO 9).

The invention further provides an antifungal peptide which comprises at least six amino acid residues identical to a run of amino acid residues in an antifungal protein according to the invention, said run of residues including at least one of the mutated residues.

In particular, there are provided the following antifungal proteins and antifungal peptides derived therefrom:

a protein having the amino acid sequence of Rs-AFP1 (SEQ ID NO: 8), Rs-AFP2 (SEQ ID NO: 9), Rs-AFP3 (SEQ ID NO: 10) or Rs-AFP4 (SEQ ID NO: 11) in which the glycine residue at position 9 is replaced by an arginine residue;

a protein having the amino acid sequence of Rs-AFP1 (SEQ ID NO: 8), Rs-AFP2 (SEQ ID NO: 9) or Rs-AFP3 (SEQ ID NO: 10) in which the valine residue at position 39 is replaced by an arginine residue;

a protein having the amino acid sequence of Rs-AFP4 (SEQ ID NO: 11) in which the isoleucine residue at position 39 is replaced by an arginine residue;

a protein having the amino acid sequence of Rs-APF1 (SEQ ID NO: 8), Rs-AFP2 (SEQ ID NO: 9) or Rs-AFP3 (SEQ ID NO: 10) in which the glycine residue at position 9 is replaced by an arginine residue and the valine residue at position 39 is replaced by an arginine residue;

a protein having the amino acid sequence of Rs-AFP4 (SEQ ID NO: 11) in which the glycine residue at position 9 is replaced by an arginine residue and the isoleucine residue at position 39 is replaced by an arginine residue;

a protein having the amino acid sequence of Rs-AFP1 (SEQ ID NO: 8), Rs-AFP3 (SEQ ID NO: 10) or Rs-AFP4 (SEQ ID NO: 11) in which the glutamic acid residue at position 5 is replaced by a methionine residue;

a protein having the amino acid sequence of Rs-AFP2 (SEQ ID NO: 9)in which the glutamine residue at position 5 is replaced by a methionine residue;

a protein having the amino acid sequence of Rs-AFP1 (SEQ ID NO: 8), RS-AFP2 (SEQ ID NO: 9), Rs-AFP3 (SEQ ID NO: 10) or Rs-AFP4 (SEQ ID NO: 11) in which the glycine residue at position 16 is replaced by a methionine residue.

Proteins according to the invention include proteins having one of the following sequences:

QKLCERPSRTWSGVCGNNNACKNQCIN-LEKARHGSCNYVFPAHKCICYFPC (SEQ ID NO: 57);
QKLCERPSGTWSGVCGNNNACKNQCIN-LEKARHGSCNYRFPAHKCICYFPC (SEQ ID NO: 58);
QKLCERPSRTWSGVCGNNNACKNQCIN-LEKARHGSCNYRFPAHKCICYFPC (SEQ ID NO: 59);
QKLCMRPSGTWSGVCGNNNACKNQCIN-LEKARHGSCNYVFPAHKCICYFPC (SEQ ID NO: 60);
QKLCERPSGTWSGVCMNNNACKNQCIN-LEKARHGSCNYVFPAHKCICYFPC (SEQ ID NO: 61);
QKLCQRPSRTWSGVCGNNNACKNQCIR-LEKARHGSCNYVFPAHKCICYFPC (SEQ ID NO: 62);
QKLCQRPSGTWSGVCGNNNACKNQCIR-LEKARHGSCNYRFPAHKCICYFPC (SEQ ID NO: 63);
QKLCQRPSRTWSGVCGNNNACKNQCIR-LEKARHGSCNYRFPAHKCICYFPC (SEQ ID NO: 64);
QKLCMRPSGTWSGVCGNNNACKNQCIR-LEKARHGSCNYVFPAHKCICYFPC (SEQ ID NO: 65);
QKLCQRPSGTWSGVCMNNNACKNQCIR-LEKARHGSCNYVFPAHKCICYFPC (SEQ ID NO: 66);
KLCERSSRTWSGVCGNNNACKNQCIRLE-GAQHGSCNYVFPAHKCICYFPC (SEQ ID NO: 67);
KLCERSSGTWSGVCGNNNACKNQCIRLE-GAQHGSCNYRFPAHKCICYFPC (SEQ ID NO: 68);
KLCERSSRTWSGVCGNNNACKNQCIRLE-GAQHGSCNYRFPAHKCICYFPC (SEQ ID NO: 69);
KLCMRSSGTWSGVCGNNNACKNQCIRLE-GAQHGSCNYVFPAHIKCICYFPC (SEQ ID NO: 70);
KLCERSSGTWSGVCMNNNACKNQCIRLE-GAQHGSCNYVFPAHKCICYFPC (SEQ ID NO: 71);
QKLCERSSRTWSGVCGNNNACKNQCIN-LEGARHGSCNYFPYHRCICYFPC (SEQ ID NO: 72);
QKLCERSSGTWSGVCGNNNACKNQCIN-LEGARHGSCNYRFPYHRCICYFPC (SEQ ID NO: 73);
QKLCERSSRFWSGVCGNNNACKNQCIN-LEGARHGSCNYRFPYHRCICYFPC (SEQ ID NO: 74);
QKLCMRSSGTWSGVCGNNNACKNQCIN-LEGARHGSCNYIFPYHRCICYFPC (SEQ ID NO: 75);
QKLCERSSGTWSGVCMNNNACKNQCIN-LEGARHGSCNYIFPYHRCICYFPC (SEQ ID NO: 76).

A cDNA clone encoding the plant-derivable "wild-type" Rs-AFP2 preprotein was modified by recombinant DNA methods in order to allow expression in the yeast *Saccharomyces cerevisiae*. This peptide was expressed in yeast as a fusion protein carrying at its N-terminus the prepro sequences derived from the precursor of the yeast pheromone mating factor α1. These sequences allow secretion of the biologically active peptide in a correctly processed form. The yeast expression system was then used to express and characterize isoforms of the Rs-AFP2 protein by introducing deliberate or random changes into the coding region. These isoforms were subsequently purified and tested for their antifungal activity.

The Rs-AFP2 isoform having a mutation at position 5 (glutamine to methionine) (SEQ ID NO: 22) and the Rs-AFP2 isoform having a mutation at position 16 (glycine to methionine) (SEQ ID NO: 25) have an enhanced salt-tolerant antifungal activity. However, two other isoforms were found to possess particularly advantageous antifungal properties. The Rs-AFP2 isoform having a mutation at position 9 (glycine to arginine) (SEQ ID NO: 38) and the Rs-AFP2 isoform having a mutation at position 39 (valine to arginine) (SEQ ID NO: 43) have a significantly enhanced antifungal activity. This enhanced activity is prominent in high salt conditions. An Rs-AFP2 isoform having a mutation at both position 9 (glycine to arginine) and at position 39 (valine to arginine) may have an even greater salt-tolerance.

Proteins which maintain their antifungal activity as salt concentration is increased are particularly suitable for use as antifungal agents in higher salt conditions. For example, such proteins are particularly suitable for expression within some biological organisms including plants. The most abundant divalent cations in plant tissues are $Ca^{2+}$ and $Mg^{2+}$. The concentration of free $Ca^{2+}$ in the cytosol is very low (0.1 to 1 μM) (Macklom, 1984, Plant Cell Environ. 7:407–413)), whereas free $Mg^{2+}$ reaches about 1 mM (Hepler and Wyne, 1982, Ann Rev Plant Physiol, 36:397–439). Free $Ca^{2+}$ in plant vacuoles is about 0.06 to 1 mM and apoplastic free $Ca^{2+}$ ranges between 0.02 and 1.3 mM (Harker and Venis, 1991, Plant Cell Environ, 14:525–530). It thus appears that relatively high ionic strength conditions occur in all cellular compartments. In many cases, however, fungal infection leads to the disruption of the cells and contact of the cellular contents with the environment. Therefore it is difficult to predict the exact ionic conditions under which antifungal proteins expressed within a plant cell will interact with invading hyphae. However, proteins whose antifungal activity is less sensitive to cation concentration are particularly suitable for expression within plant cells.

An antifungal protein according to the invention may be manufactured from its known amino acid sequence by chemical synthesis using a standard peptide synthesiser, or produced within a suitable organism (for example, a microorganism or plant) by expression of recombinant DNA. The antifungal protein is useful as a fungicide and may be used for agricultural or pharmaceutical applications.

Knowledge of its primary structure enables manufacture of the antifungal protein, or parts thereof, by chemical synthesis using a standard peptide synthesiser. It also enables production of DNA constructs encoding the antifungal protein.

The invention further provides a DNA sequence encoding an antifungal protein according to the invention. The DNA sequence may be predicted from the known amino acid sequence and DNA encoding the protein may be manufactured using a standard nucleic acid synthesiser. Alternatively, DNA encoding proteins according to the invention may be produced by appropriate site-directed mutagenesis of DNA sequences encoding one of the proteins shown in FIG. 1.

The DNA sequence encoding the antifungal protein may be incorporated into a DNA construct or vector in combination with suitable regulatory sequences (promoter, terminator, transit peptide etc). The DNA sequence may be placed under the control of a homologous or heterologous promoter which may be a constitutive or an inducible promoter (stimulated by, for example, environmental conditions, presence of a pathogen, presence of a chemical). The transit peptide may be a homologous or heterologous to the antifungal protein and will be chosen to ensure secretion to the desired organelle or to the extracellular space. The transit peptide is preferably that naturally associated with the antifungal protein of interest.

Such a DNA construct may be cloned or transformed into a biological system which allows expression of the encoded protein or an active part of the protein. Suitable biological systems include micro-organisms (for example, bacteria such as *Escherichia coli,* Pseudomonas and endophytes such as *Clavibacter xyli* subsp. *cynodontis* (Cxc); yeast; viruses; bacteriophages; etc), cultured cells (such as insect cells, mammalian cells) and plants. In some cases, the expressed protein may subsequently be extracted and isolated for use.

An antifungal protein according to the invention is useful for combatting fungal diseases in plants. The invention further provides a process of combating fungi whereby they are exposed to an antifungal protein according to the invention.

For pharmaceutical applications, the antifungal protein may be used as a fungicide to treat mammalian infections (for example, to combat yeasts such as Candida).

An antifungal protein according to the invention may also be used as a preservative (for example, as a food additive).

For agricultural applications the antifungal protein may be used to improve the disease-resistance or disease-tolerance of crops either during the life of the plant or for post-harvest crop protection. Pathogens exposed to the proteins are inhibited. The antifungal protein may eradicate a pathogen already established on the plant or may protect the plant from future pathogen attack. The eradicant effect of the protein is particularly advantageous.

Exposure of a plant pathogen to an antifungal protein may be achieved in various ways, for example:

(a) The isolated protein may be applied to plant parts or to the soil or other growth medium surrounding the roots of the plants or to the seed of the plant before it is sown using standard agricultural techniques (such as spraying).

The protein may have been extracted from plant tissue or chemically synthesised or extracted from microorganisms genetically modified to express the protein. The protein may be applied to plants or to the plant growth medium in the form of a composition comprising the protein in admixture with a solid or liquid diluent and optionally various adjuvants such as surface-active agents. Solid compositions may be in the form of dispersible powders, granules, or grains.

(b) A composition comprising a micro-organism genetically modified to express the antifungal protein may be applied to a plant or the soil in which a plant grows.

(c) An endophyte genetically modified to express the antifungal protein may be introduced into the plant tissue (for example, via a seed treatment process).

An endophyte is defined as a micro-organism having the ability to enter into non-pathogenic endosymbiotic relationships with a plant host. A method of endophyte-enhanced protection of plants has been described in a series of patent applications by Crop Genetics International Corporation (for example, International Application Publication Number WO90/13224 European Patent Publication Number EP-125468-B1, International Application Publication Number WO91/10363, International Application Publication Number WO87/03303). The endophyte may be genetically modified to produce agricultural chemicals. International Patent Application Publication Number WO94/16076 (ZENECA Limited) describes the use of endophytes which have been genetically modified to express a plant-derived antifungal protein.

(d) DNA encoding an antifungal protein may be introduced into the plant genome so that the protein is expressed within the plant body (the DNA may be cDNA, genomic DNA or DNA manufactured using a standard nucleic acid synthesiser).

Plant cells may be transformed with recombinant DNA constructs according to a variety of known methods (Agrobacterium Ti plasmids, electroporation, microinjection, microprojectile gun, etc). The transformed cells may then in suitable cases be regenerated into whole plants in which the new nuclear material is stably incorporated into the genome. Both transformed monocotyledonous and dicotyledonous plants may be obtained in this way, although the latter are usually more easy to regenerate. Some of the progeny of these primary transformants will inherit the recombinant DNA encoding the antifungal protein(s).

The invention further provides a plant having improved resistance to a fungal pathogen and containing recombinant DNA which expresses an antifungal protein according to the invention. Such a plant may be used as a parent in standard plant breeding crosses to develop hybrids and lines having improved fungal resistance.

Recombinant DNA is DNA, preferably heterologous, which has been introduced into the plant or its ancestors by transformation. The recombinant DNA encodes an antifungal protein expressed for delivery to a site of pathogen attack (such as the leaves). The DNA may encode an active subunit of an antifungal protein.

A pathogen may be any fungus growing on, in or near the plant. In this context, improved resistance is defined as enhanced tolerance to a fungal pathogen when compared to a wild-type plant. Resistance may vary from a slight increase in tolerance to the effects of the pathogen (where the pathogen in partially inhibited) to total resistance so that the plant is unaffected by the presence of pathogen (where the pathogen is severely inhibited or killed). An increased level of resistance against a particular pathogen or resistance against a wider spectrum of pathogens may both constitute an improvement in resistance. Transgenic plants (or plants derived therefrom) showing improved resistance are selected following plant transformation or subsequent crossing.

Where the antifungal protein is expressed within a transgenic plant or its progeny, the fungus is exposed to the protein at the site of pathogen attack on the plant. In particular, by use of appropriate gene regulatory sequences, the protein may be produced in vivo when and where it will be most effective. For example, the protein may be produced within parts of the plant where it is not normally expressed in quantity but where disease resistance is important (such as in the leaves).

Examples of genetically modified plants which may be produced include field crops, cereals, fruit and vegetables such as: canola, sunflower, tobacco, sugarbeet, cotton, soya, maize, wheat, barley, rice, sorghum, tomatoes, mangoes, peaches, apples, pears, strawberries, bananas, melons, potatoes, carrot, lettuce, cabbage, onion.

BRIEF DESCRIPTION OF THE FIGURES AND EXAMPLE

The invention will now be described by way of example only, with reference to the following drawings wherein:

FIG. 1 shows the amino acid sequences of the Rs-AFPs and related proteins. In FIG. 1, the proteins have the following sequence identifications: Rs-AFP1-SEQ ID NO: 8; Rs-AFP2-SEQ ID NO: 9; Rs-AFP3-SEQ ID NO: 10; Rs-AFP4-SEQ ID NO: 11; Br-AFP1-SEQ ID NO: 12; Br-AFP2-SEQ ID NO: 13: Bn-AFP1-SEQ ID NO: 14; Bn-AFP2-SEQ ID NO: 15; Sa-AFP1-SEQ ID NO: 16; Sa-AFP2-SEQ ID NO: 17; and At-AFP1-SEQ ID NO: 18.

FIG. 2 shows the nucleotide sequence of the cDNA encoding Rs-AFP1 (SEQ ID NO: 19).

FIG. 4 shows the amino acid sequences of plant-derivable Rs-AFP2, and a series of yeast-expressed Rs-AFP2 (yRs-AFP2) isoforms. In FIG. 4 the proteins have the following sequence identifications:

| Protein | SEQ ID NO: |
|---|---|
| Rs-AFP2 | SEQ ID NO: 77 |
| yRs-AFP2 | SEQ ID NO: 20 |
| SIα2 | SEQ ID NO: 21 |
| yRs-AFP2/Q5M | SEQ ID NO: 22 |
| yRs-AFP2/T10G | SEQ ID NO: 23 |
| yRs-AFP2/W11S | SEQ ID NO: 24 |
| yRs-AFP2/G16M | SEQ ID NO: 25 |
| yRs-AFP2/A31W | SEQ ID NO: 26 |
| yRs-AFP2/Y38G | SEQ ID NO: 27 |
| yRs-AFP2/F40M | SEQ ID NO: 28 |
| yRs-AFP2/K44Q | SEQ ID NO: 29 |
| yRs-AFP2/Y48I | SEQ ID NO: 30 |
| yRs-AFP2/T10A | SEQ ID NO: 31 |
| yRs-AFP2/H33A | SEQ ID NO: 32 |
| yRs-AFP2/Y38A | SEQ ID NO: 33 |
| yRs-AFP2/F40A | SEQ ID NO: 34 |
| yRs-AFP2/P7- | SEQ ID NO: 35 |
| yRs-AFP2/P41- | SEQ ID NO: 36 |
| yRs-AFP2/P7R | SEQ ID NO: 37 |
| yRs-AFP2/G9R | SEQ ID NO: 38 |
| yRs-AFP2/S12R | SEQ ID NO: 39 |
| yRs-AFP2/I26R | SEQ ID NO: 40 |
| yRs-AFP2/L28R | SEQ ID NO: 41 |
| yRs-AFP2/N37R | SEQ ID NO: 42 |
| yRs-AFP2/V39R | SEQ ID NO: 43 |
| yRs-AFP2/A42R | SEQ ID NO: 44 |
| yRs-AFP2/I46R | SEQ ID NO: 45 |
| yRs-AFP2/F49R | SEQ ID NO: 46 |

FIG. 5 illustrates PCR amplification using the mutagenic primer OWB41 and the MB13 reverse primer. In FIG. 5, the primers have the following sequence identifications: OWB41-SEQ ID NO: 47; OWB42-SEQ ID NO: 48; OWB43-SEQ ID NO: 49; OWB44-SEQ ID NO: 50; OWB45-SEQ ID NO: 51; OWB77-SEQ ID NO: 52; OWB47-SEQ ID NO: 53; OWB48-SEQ ID NO: 55; OWB49-SEQ ID NO: 54; OWB50-SEQ ID NO: 56.

Figure 6:
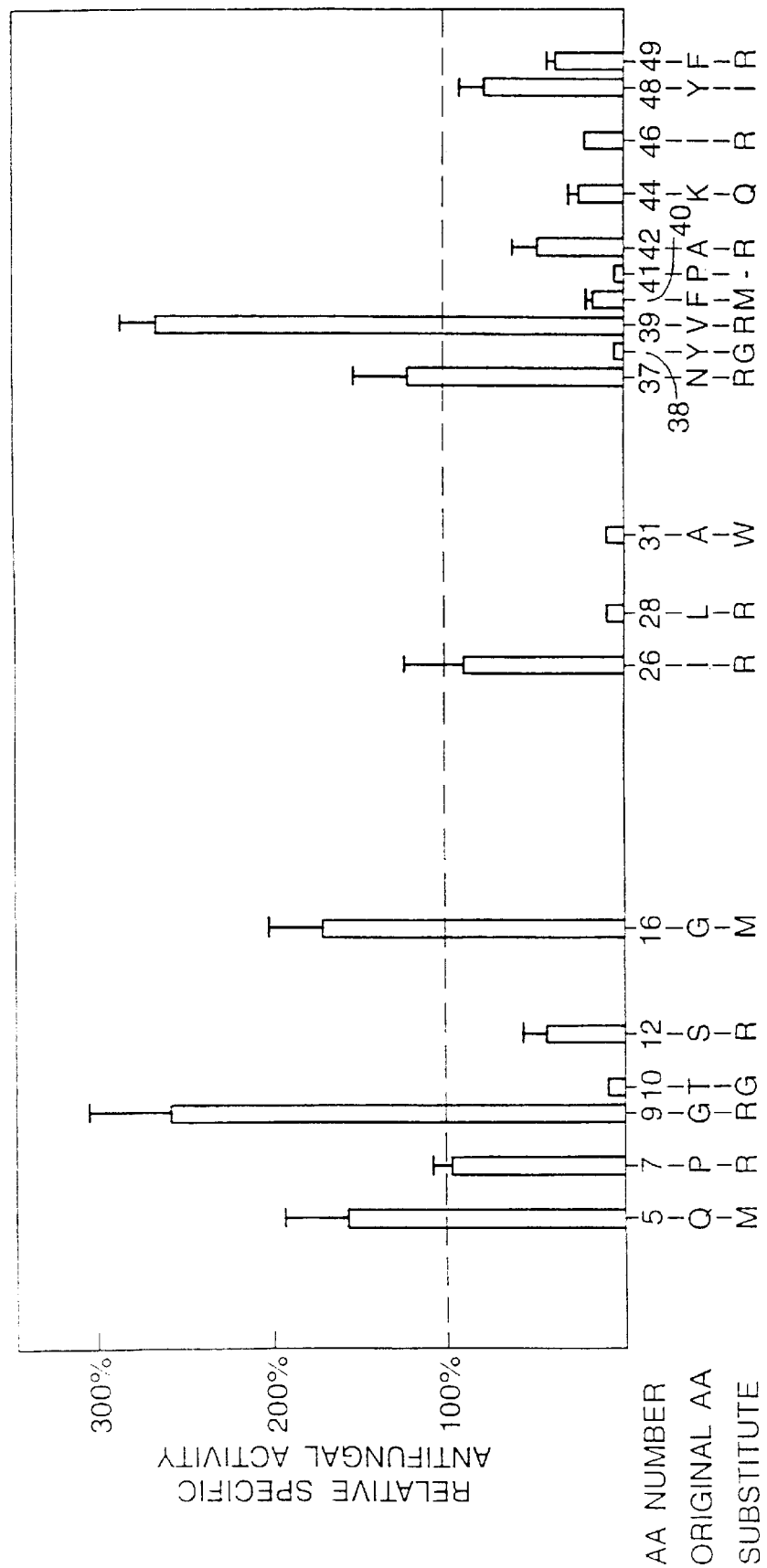

FIG. 6 is a graph of relative specific antifungal activity ($1/IC_{50}$) on F culmorum of the Rs-AFP isoforms. In FIG. 6, the peptides have the following sequence identifications: Q5M-SEQ ID NO: 22; P7R-SEQ ID NO: 37; G9R-SEQ ID NO: 38; T10G-SEQ ID NO: 23; S12R-SEQ ID NO: 39; G16M-SEQ ID NO: 25; I26R-SEQ ID NO: 40; L28R-SEQ ID NO: 41; A31W-SEQ ID NO: 26; N37R-SEQ ID NO: 42; Y38G-SEQ ID NO: 27; V39R-SEQ ID NO: 43; F40M-SEQ ID NO: 28; P41-SEQ ID NO: 36; A42R-SEQ ID NO: 44; K44Q-SEQ ID NO: 29; I46R-SEQ ID NO: 45; Y48I-SEQ ID NO: 30; F49R-SEQ ID NO: 46.

FIG. 7 is a graph of the percentage growth inhibition of F culmorum caused by Rs-AFP2 isoforms in varying concentrations of $CaCl_2$ (panel A) and KCl (panel B).

EXAMPLE 1

Construction of Expression Vectors for Secretion of Rs-AFP2 by Yeast

Saccharomyces cerevisiae can be used as a vector for the production and secretion of Rs-AFP2 as described by Vilas Alves et al, FEBS Lett, 1994, 348:228–232 using the method described below.

Plasmid pFRG1 is a pBluescript IISK derivative containing a full length cDNA clone encoding Rs-AFP1 (international patent application publication number WO93/05153). By PCR-mediated site-directed mutagenesis (Merino et al, 1992, BioTechniques, 12:508–510) two mutations were introduced such that the encoded protein is the more active isoform Rs-AFP2. A third mutation (CGA to CGT for $Arg^{31}$ of mature Rs-AFP2) was introduced to comply with the codon usage preference in Saccharomyses cerevisiae (Bennetzen and Hall, 1982, J Biol Chem, 257:3026). The resulting plasmid was called pBluescript/RsAFP2.

The vectors pMFpre/RsAFP2 and pMFprepro/RsAFP2 are based on the yeast/E coli shuttle vector pTG3828 (Achstetter et al, 1992, Gene, 110:25–31). pTG3828 contains a URA3-d selection marker, the origin of replication from the yeast $2\mu$ plasmid, the prokaryotic ColE1 origin of replication and the ampicillin resistance marker from pBR322. pTG3828 also contains the yeast phosphoglycerate kinase (PGK) terminator preceded by a polylinker with multiple unique restriction sites which facilitate insertion of an expression block.

The expression blocks in pMFpre/RsAFP2 and pMF prepro/RsAFP2 were derived from the M13 phage derivative M13TG5879 (Reichhart et al, 1999, Invertebrate Reproduction and Development, 21:15–24) which contains the promoter of the yeast MFα1 gene, the coding region of the MFα1 pre-sequence with an engineered NheI site, and the coding region of the MFα1 pro-sequence with an engineered HindIII site. The expression cassette of M13TG5879 was amplified by PCR using the sense primer OWB63: 5'TATCA GTCGACGCATGCTATTGATAAGATTTAAAGG SEQ ID NO: 1 (SalI site underlined, SphI site in bold), which introduces a novel SalI site immediately adjacent to the SphI site at the 5' end of the MFα1 promoter, and the M13 reverse primer as an antisense primer. The resulting PCR product was digested with SalI-BamHI and subcloned into pBluescriptII SK to yield pVD4.

Plasmid pBluescript/RsAFP2 was used as a template for the amplification of the coding sequence of mature Rs-AFP2 in two separate PCR reactions. In the first PCR reaction the sense primer OWB61:

5'AAT AAGCTTGGACAAGAGACAGAAGTTGTGCCAAAGG (SEQ ID NO: 2) (HindIII site underlined) was designed such that sixteen extra nucleotides (coding for the last five amino acids of the MFα1 pro-sequence) were added upstream of the coding region of mature Rs-AFP2. The HindIII site allowed in frame cloning into the HindIII site in the MFα1 prosequence region of pVD4 Reichhart J M et al, 1991, Invertebrate Reproduction and Development 21:15–24). The antisense primer OWB64: 5'AA GGATCCCTATTAACAAGGAAAGTAGC (SEQ ID NO: 3) (BamHI site underlined) introduced a second stop codon and a BamHI site immediately downstream of the stop codon of the coding region of Rs-AFP2. In the second PCR reaction, the same antisense primer was combined with the sense primer OWB62: 5'AAT GCTAGCTCAGAAGTTGTGCCAAAGG (SEQ ID NO: 4) (NheI site underlined) which added seven extra nucleotides (coding for the last two amino acids of the MFα1 presequence), including a NheI site (for in frame cloning into the NheI site in the MFα1 presequence region of pVD4) upstream of the coding region of mature Rs-AFP2. The fragments corresponding to the mature domain of Rs-AFP2 obtained by PCR amplification in the first or in the second reaction were digested with HindIII-BamH1 and NheI-BamHI, respectively, and introduced in the corresponding sites of pVD4 to yield vectors pVD5 and pVD6, respectively. The resulting vectors were digested with SalI-BamHI to isolate the expression blocks, which were then subcloned into SalI-BglII digested pTG3828 to yield the vectors pMFpre-RsAFP2 and pMFprepro/RSAFP2, respectively.

Figure 3:
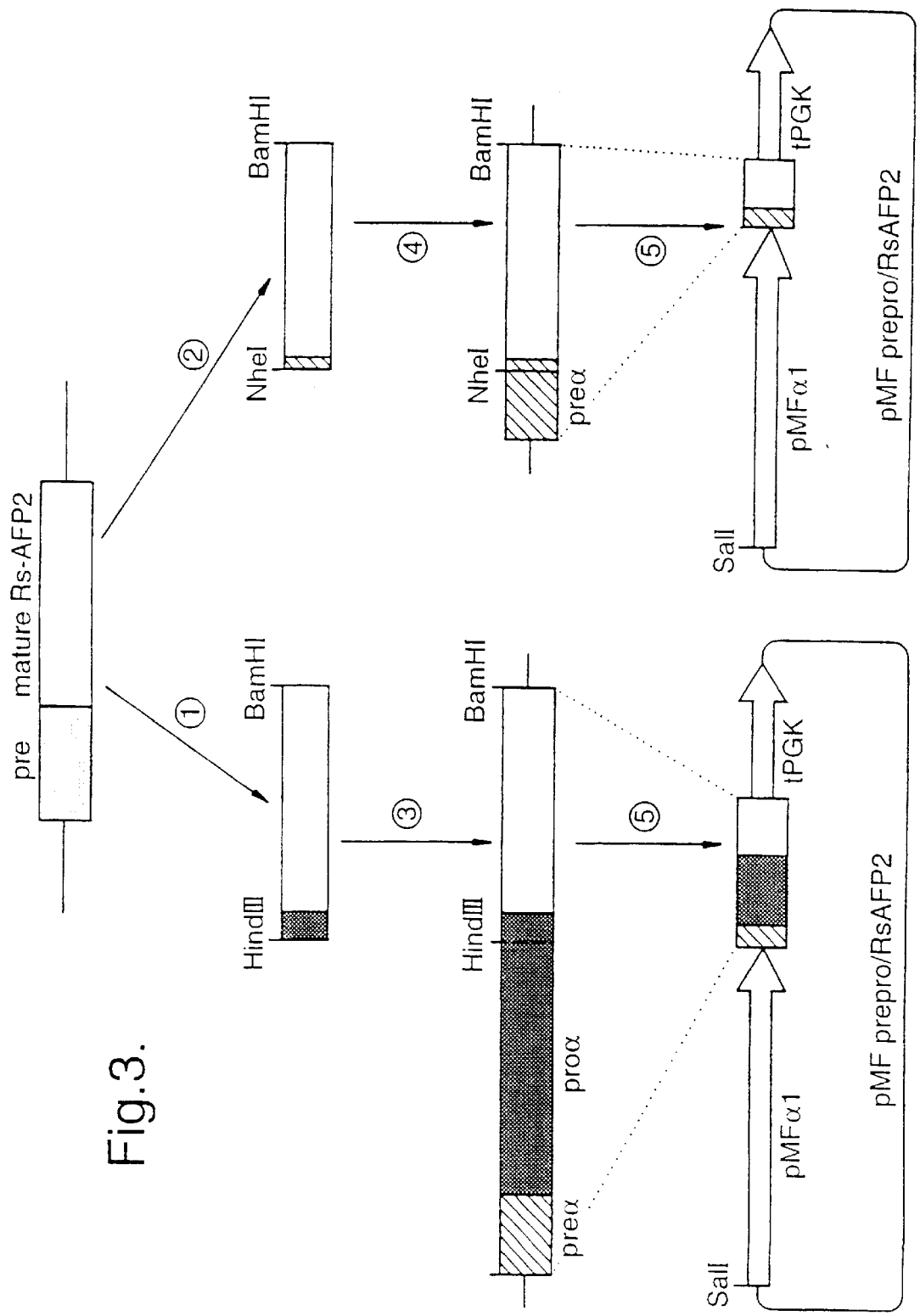
FIG. 3 shows the schematic representation of the construction of the expression vectors pMF prepro/RsAFP2 and pMFpre/RsAFP2.

FIG. 3 shows the schematic representation of the construction of the expression vectors pMFprepro/RsAFP2 and pMFpre/RsAFP2. The different steps in the procedure are (1) PCR amplification of the coding region of mature RsAFP2 using primers to add a HindIII site and part of the MFα1 pro region (5' site) and a BamHI site (3' site); (2) PCR amplification of the coding region of mature RsAFP2 using primers to introduce a NheI and part of the MFα1 pre region (5' site) and a BamHI (3' site); (3) subcloning of the PCR product into HindIII-BamHI digested pVD4; (4) subcloning of the PCR product into NheI-BamHI digested pVD4; (5) digestion of the resulting plasmids with SalI/BamHI and subcloning of the inserts in SalI-BglII digested pTG3828. (Abbreviations in FIG. 3: pre, signal sequence domain of RsAFP1 cDNA; preα, signal sequence domain of MFα1 gene; proα, propeptide domain of MFα1 gene; pMFα1, promoter domain of MFα1 gene; tPGK, terminator domain of the yeast phosphoglycerate kinase gene).

The plasmids pMFpre-RsAFP2, pMFprepro/RSAFP2 and pTG3828 were transformed in yeast (*S cerevisiae*) strain c13-ABYS86 (genotype; α pra1-1, prb1-1, prc1-1, cps1-3, ura3-5, leu2-3, 112, his-) by the lithium acetate method as described by Elble (1992, BioTechniques, 13:18). Selection of transformants was done on minimal selective SD medium lacking uracil (Sherman, 1991. Meth Enzymnol. 194:3–21). Presence of the plasmids in the yeast colonies was verified by PCR as described by Ward (1990, NucI Acids Res, 18:5319).

EXAMPLE 2

Purification and Analysis of Yeast-Expressed Rs-AFP2

Yeast cells transformed with either pTG3828, pMFprepro/Rs AFP2 or PMFpre/RsAFP2 were grown in selective SD medium until a saturated culture was obtained. To assess the antifungal activity of proteins secreted by the yeast cells, the supernatant of the yeast cultures was filtered (sterile 0.22 μm filter) and serially diluted in sterile water. Diluted samples (20 μl) were incubated in microtiter plate wells with 80 μl of half strength potato dextrose broth (Difco) containing spores $10^4$ spores/ml) of *Fusarium culmorum*.

Growth of the fungi was monitored by microspectrophotometry as described by Broekaert et al (1990, FEMS Microbiol Lett, 69:55–60). Homogenates of yeast cells were prepared by spinning down 1 ml of a saturated yeast culture, suspending the cells in 200 μl of water, vortexing the cells in the presence of 0.2 g of glass beads (425–600 μm), and clearing the homogenate by centrifugation (1 min, 10000× g). Antifungal activity could only be detected in the culture medium of yeast cells transformed with pMFprepro/RsAFP2, which contained about 2 μg/ml of Rs-AFP2 equivalents. The activity of the homogenate of these cells, as well as that of culture media and cell homogenates of yeast cells transformed with pMFpre/RsAFP2 or pTG3828 transformed yeasts was below the detection limit (about 0.2 μg/ml of Rs-AFP2 equivalents). Hence, pMFprepro/RsAFP2 seems to convey significant expression of Rs-AFP2 in yeast.

The supernatant of 100 ml of a saturated culture of yeast transformed with pMFprepro/RSAFP2 (grown on minimal selective SD medium supplemented with 0.5% w/v of casamino acids) was centrifuged (4000 rpm, 10 min), and filtered (0.45 μm) to remove yeast cells and debris. Tris-HCl (pH9) was added to the supernatant to a final concentration of 50 mM. The sample was loaded at a flow rate of 2 ml/min on an anion exchange chromatography column (Q-Sepharose Fast Flow, 20 ml bed volume, Pharmacia), on-line connected with a disposable reversed-phase C8 silica column (Bond Elut, 500 mg solid phase, Varian, Harbor City, USA). The antifungal activity was not retained on the Q-Sepharose matrix but bound to the C8 silica matrix. The C8 silica column was rinsed with 6 ml of 10% (v/v) acetonitrile in 0.1% (v/v) trifluroacetic acid (TFA) and subsequently eluted with 4 ml of 30% (v/v) acetonitrile in 0.1% (v/v) TFA. The latter eluate was dried in a rotating vacuum concentrator, redissolved in 0.5 ml 15% (v/v) acetonitrile containing 0.1% (v/v) TFA, and was loaded on a reversed-phase C2/C18 silica column (Pep-S, 5 μm beads, 0.4×25 cm, Pharmacia connected to a Waters 600 HPLC station pre-equilibriated with 15% acetonitrile containing 0.1% (v/v) TFA. After loading, the column was rinsed with the same buffer until the absorbance reached background level. The column was subsequently eluted with a 15 minute linear gradient from 15% to 50% acetonitrile containing 0.1% TFA at a flow rate of 1 ml/min. The eluate was monitored for proteins by on-line measurement of the absorbance at 280 nm. Peak fractions were collected manually, dried in a rotating vacuum concentrator to remove the solvents, and redissolved in 200 μl of distilled water. Twenty μl fractions were tested in a liquid growth inhibition assay: 20 μl samples were incubated in microtiter plate wells with 80 μl of half strength potato dextrose broth (Difco) containing $10^4$ spores/ml of *F culmorum*; growth of the fungi was monitored by microspectrophotometry as described by Broekaert et al (1990, FEMS Microbiol Lett, 69: 55–60).

Only the main peak (peak A, elution time 14.7 min) and a smaller peak (peak B, elution time 15.2 min) coeluted with antifungal activity. The elution time of peak B was identical to that of plant-derivable Rs-AFP2 (15.2 min).

The amino-terminal amino acid sequence obtained by automated Edman degradation for RPC-purified peak A revealed a sequence of 51 amino acids, all of which being identical to the sequence of Rs-AFP2. This sequence includes an N-terminal glutamine which is known to be blocked by cyclisation in plant-derivable Rs-AE P2 (Teinas et al, 1992, J Biol Chem, 267:15301–15309). Absence of any contaminating signals in the amino acid sequence analysis indicated that the peak A fraction was essentially homogeneous. No sequence signals could be recorded for RPC-purified peak B material, probably due to blocking of its N-terminus. This protein fraction was treated with pyroglutamate aminopeptidase in order to cleave off the presumed blocked glutamine residue, but also in this case no amino acid sequence could be determined, whereas the same treatment successfully deblocked plant-derivable Rs-AFP2. Because of the uncertain identification of the peak B material and because of its lower abundancy relative to peak A material, the peak B material was not further analysed.

The specific antifungal activity of RPC-purified peak A material as well as that of plant-derivable Rs-AFP2, was determined by measuring the percentage growth inhibition of *F culmorum* caused by serial dilutions of the protein samples. The $IC_{50}$ values (concentration required for 50% growth inhibition) values derived from dose-response curves, was about 3 µg/ml for both protein preparataions. Moreover, the type of inhibition caused by RPC-purified peak A material was identical to that caused by plant-derivable Rs-AFP2, showing a characteristic morphological distortion of the fungal hyphac typified by the induction of multiple branches near the tips.

These results show that yeast cells transformed with pMFprepro/Rs-AFP2 produce a protein that has the same biological activity as plant-derivable Rs-AFP2. Presence of the MFα1 preprosequence seems to be essential for expression of Rs-AFP2 in yeast.

EXAMPLE 3

Production of Rs-AFP2 isoforms containing amino acid mutations

In order to produce Rs-AFP2 isoforms with single amino acid substitutions or deletions, mutations were introduced by PCR-directed mutagenesis in the DNA region coding for the mature Rs-AFP2 domain.

FIG. 4 shows the amino acid sequences of plant-derivable wild-type protein (Rs-AFP2) (SEQ ID NO: 77), yeast-expressed Rs-AFP2 (yRs-AFP2) (SEQ ID NO: 20), *Sorghum bicolor* α-amylase inhibitor 2 (SIα2) (SEQ ID NO: 21) and four series of yeast-expressed isoforms of Rs-AFP2 with single amino acid substitutions or deletions. Z indicates a pyroglutamyl residue. Amino acids identical to the corresponding residue in Rs-AFP2 are indicated by dots whereas amino acid deletions relative to the Rs-AFP2 sequence are represented by a dash.

The yRS-AFP2 isoforms in Series A (FIG. 4) include a range of mutations in Rs-AFP2, some of which represent a substitution by the corresponding amino acid occurring in SIα2 (Bloch and Richardson, 1991, FEBS Lett, 279:101–104). SIα2 is a protein which is partially homologous to Rs-AFP2 but which (in contrast to Rs-AFP2) does not exhibit antifungal activity when assayed as described in Example 2. Series B contains proline deletions. In Series C, particular amino acids were replaced by a basic residue (arginine) in order to obtain more basic Rs-AFP2 isoforms.

The vector for production of yRS-AFP/Q5M, the Rs-AFP2 isoform with an amino acid substitution at position 5 (glutamine to methionine) was prepared as follows. The vector pVD5 (see Example 1) was used as a template for PCR amplification using the mutagenic primer OWB41 (SEQ ID NO: 47) and the M13 reverse primer (5'AGGAAACAGCTATGACCATG) (SEQ ID NO: 5). FIG. 5 illustrates PCR amplification using the mutagenic primer OWB41 and the M13 reverse primer. The resulting PCR product was digested with HindIII and Bam HI and subcloned into the corresponding sites of pVD4 (see Example 1). The resulting vector was digested with SalI and Bam HI and subcloned into SalI-BglII dioested yeast transformation vector pTG3828 (see Example 1).

The vectors for the production of Rs-AFP2 isoforms other than yRs-AFP2/Q5M were constructed as follows. The vector pVD5 was used as a template for introducing mutations by the two-step PCR protocol of Merino et al (1992, BioTechniques, 12:508–510), with the PCR mutagenic primers being designed according to standard molecular biology techniques. For example, for Series A and B isoforms, a first PCR reaction was performed using a mutagenic primer (either OWB42 (SEQ ID NO: 47), OWB43 (SEQ ID NO: 49), OWB44 (SEQ ID NO: 50), OWB45 (SEQ ID NO: 51), OWB77 (SEQ 11) NO: 52), OWB47 (SEQ ID NO: 53), OWB48 (SEQ ID NO: 55), OWB49 (SEQ ID NO: 54) or OWB50 (SEQ ID NO: 56): see FIG. 5) and the primer OWB35 (5'GGAATAGCCGATGGAGATCT AGGAAAACAGCTATGACCATG (SEQ ID NO: 6), nucleotides corresponding to the M13 reverse primer underlined). The resulting PCR product was used in a second PCR reaction as a megaprimer and after 5 amplification cycles the primers OWB61 (see Example 1) and OWB36 (GGAATACCCGATCGAGATCTAGGA (SEQ ID NO: 7), corresponding to the first 24 nucleotides of OWB 35) were added. The PCR product of the second PCR reaction was subcloned in pVD4 and subsequently in pTG3828 as described above. Nucleotide sequences of all subcloned PCR products were verified by nucleotide sequencing. The obtained derivatives of pTG3828 were transformed into yeast and the RsAFP2 isoforms produced by the transformed yeast strains was purified by reversed-phase chromatography (RPC) as described in Example 2. All Rs-AFP2 isoforms had the same electrophoretic mobility as plant-derivable wild-type Rs-AFP2.

An Rs-AFP2 isoform having a mutation at both position 9 (glycine to arginine) and at position 39 (valine to arginine) may be readily made in yeast using either the G9R construct or the V39R construct as the initial PCR template instead of pVD5. The appropriate mutagenic primer is used for the second amino acid change.

EXAMPLE 4

Antifungal activity of the Rs-AFP2 isoforms

In order to assess the effect of single amino acid substitutions or deletions on the antifungal activity of Rs-AFP2, yeast-expressed and RPC-purified Rs-AFP2 isoforms (see FIG. 4) were tested for their specific antifungal activity. The RPC-purified Rs-AFP2 isoforms were first analysed by SDS-PAGE and the purity of the preparations was estimated to be at least 50%.

For each isoform, two independent purifications were carried out and the antifungal activity was determined in duplicate using *F culmorum* as a test fungus in two different media: a low ionic strength medium called SMF– (Terras et al, 1992, J Biol Chem, 267:15301–15309) and the same medium supplemented with 1 mM $CaCl_2$ and 50 mM KCl called SMF+. The presence of salts in the test medium especially salts with divalent cations, reduces the specific activity of Rs-AFP2. Seed-purified as well as yeast-expressed wild type Rs-AFP2 served as a control in the assays.

Results of preliminary tests are given in Table 1 which shows the relative specific antifungal activity against *F culmorum* of yeast-expressed wild-type Rs-AFP2 (yRs-AFP2) and the mutant yRs-AFP2 isoforms. The relative specific activity is expressed as the specific activity of the mutant divided by the specific activity of yRs-AFP2 and multiplied by 100. The specific activity is expressed as the reciprocal of the $IC_{50}$ value determined on *F culmorum* after 48 hour of incubation in the presence of the proteins. The specific activity was measured in medium SMF− and SMF+.

TABLE 1

| PROTEIN | RELATIVE SPECIFIC ACTIVITY (%) IN MEDIUM | |
|---|---|---|
| | SMF− | SMF+ |
| yRs-AFP2 (SEQ ID NO. 20) | 100 | 100 |
| SERIES A | | |
| yRs-AFP2/Q5M (SEQ ID NO. 22) | 100 | 100 |
| yRs-AFP2/T10G (SEQ ID NO. 23) | 30 | <16 |
| yRs-AFP2/G16M (SEQ ID NO. 25) | 151 | 114 |
| yRs-AFP2/A31W (SEQ ID NO. 26) | 15 | <5 |
| yRs-AFP2/Y38G (SEQ ID NO. 27) | 30 | <4 |
| yRs-AFP2/F40M (SEQ ID NO. 28) | 30 | 23 |
| yRs-AFP2/K44Q (SEQ ID NO. 29) | 100 | 114 |
| yRs-AFP2/Y48I (SEQ ID NO. 30) | 38 | 114 |
| SERIES B | | |
| yRs-AFP2/P7- (SEQ ID NO. 35) | 8 | 17 |
| yRs-AFP2/P41- (SEQ ID NO. 36) | 4 | <10 |
| SERIES C | | |
| yRs-AFP2/P7R (SEQ ID NO. 37) | 33 | 84 |
| yRs-AFP2/G9R (SEQ ID NO. 38) | 116 | 285 |
| yRs-AFP2/S12R (SEQ ID NO. 39) | 67 | 31 |
| yRs-AFP2/I26R (SEQ ID NO. 40) | 76 | 82 |
| yRs-AFP2/L28R (SEQ ID NO. 41) | 39 | — |
| yRs-AFP2/N37R (SEQ ID NO. 42) | 100 | 80 |
| yRs-AFP2/V39R (SEQ ID NO. 43) | 74 | 114 |
| yRs-AFP2/A42R (SEQ ID NO. 44) | 44 | 26 |
| yRs-AFP2/I46R (SEQ ID NO. 45) | 22 | — |
| yRs-AFP2/F49R (SEQ ID NO. 46) | 18 | 22 |

It is seen that certain mutations cause a major decrease in antifungal activity while certain proteins (notably Q5M (SEQ ID NO: 22) and V39R (SEQ ID NO: 43)) maintain their antifungal activity. However, two mutations cause an increase in antifungal activity. The isoform with the G16M (SEQ ID NO: 25) mutation shows an increased activity in low salt (SMF−), although activity is not so significantly different in high salt (SMF+). The mutant G9R (SEQ ID NO: 38) is approximately three times more active than yRs-AFP2 (SEQ ID NO: 20) in high salt (SMF+), although activity is not so significantly different in low salt (SMF−).

Table 2 shows results from further comparative tests of the Rs-AFP2 isoforms in which experiments were carried out in triplicate. $IC_{50}$ values were measured after 72 hours growth in low salt (SMF−) and high salt (SMF+) media. Deviations are given as standard error of the mean (sem) based on the triplicate experiments. In SMF−, the medium without added salts, most of the derivatives show no decrease or only a minor decrease in antifungal activity, while in SMF+, the medium with added salts, there is a significant decrease in antifungal activity for several Rs-AFP2 isoforms. Substitutions that apparently have little effect on the antifungal activity in SMF− (low salt medium) include G9R, V39R, Q5M and G16M. flowever, in SMF+ (high salt medium) these four isoforms (in particular G39R and V39R) show an increased antifungal activity.

TABLE 2

| | SMF− | | SMF+ | |
|---|---|---|---|---|
| PROTEIN | $IC_{50}$ | sem | $IC_{50}$ | sem |
| yRs-AFP2 (SEQ ID NO: 20) | 2.7 | 0.6 | 8.5 | 2.7 |
| yRs-AFP2/Q5M (SEQ ID NO: 22) | 4.1 | 0.2 | 5.4 | 1.2 |
| yRs-AFP2/T10G (SEQ ID NO: 23) | 11.0 | 4.2 | >100 | |
| yRs-AFP2/W11S (SEQ ID NO: 24) | 16.0 | 5.7 | >100 | |
| yRs-AFP2/G16M (SEQ ID NO: 25) | 2.2 | 0.3 | 5.0 | 0.9 |
| yRs-AFP2/A31W (SEQ ID NO: 26) | | 30.0 | 5.0 | >100 |
| yRs-AFP2/H33A (SEQ ID NO: 32) | 32.0 | 8.7 | >100 | |
| yRs-AFP2/Y38G (SEQ ID NO: 27) | 42.0 | | 17.0 | >200 |
| yRs-AFP2/F40M (SEQ ID NO: 28) | 16.0 | 6.7 | 54.0 | 13.0 |
| yRs-AFP2/P41- (SEQ ID NO: 36) | 100.0 | 15.0 | >200 | |
| yRs-AFP2/K44Q (SEQ ID NO: 29) | 3.6 | 0.4 | 36.0 | 9 |
| yRs-AFP2/Y48I (SEQ ID NO: 30) | 9.3 | 1.0 | 11.0 | 2.0 |
| yRs-AFP2/P7R (SEQ ID NO: 37) | 6.8 | 2.4 | 8.8 | 1.0 |
| yRs-AFP2/G9R (SEQ ID NO: 38) | 3.0 | 0.5 | 3.3 | 0.6 |
| yRs-AFP2/S12R (SEQ ID NO: 39) | 3.5 | 1.0 | 20.0 | 6.0 |
| yRs-AFP2/I26R (SEQ ID NO: 40) | 7.2 | 0.8 | 9.6 | 3.7 |
| yRs-AFP2/L28R (SEQ ID NO: 41) | 6.4 | 1.4 | >100 | |
| yRs-AFP2/N37R (SEQ ID NO: 42) | 2.8 | 0.3 | 7.0 | 1.8 |
| yRs-AFP2/V39R (SEQ ID NO: 43) | 4.0 | 0.2 | 3.2 | 0.3 |
| yRs-AFP2/A42R (SEQ ID NO: 44) | 4.2 | 2.5 | 18.0 | 5.2 |
| yRs-AFP2/I46R (SEQ ID NO: 45) | 12.0 | 2.4 | >40 | |
| yRs-AFP2/F49R (SEQ ID NO: 46) | 22.0 | 4.8 | 23.0 | 3.0 |

FIG. 6 is a graph of relative specific antifungal activity of the Rs-AFP isoforms as determined on *F culmorum* in medium SMF+. The specific antifungal activity ($1/IC_{50}$) of Rs-AFP2 was set at 100. Bars without indication of standard deviation represent maximum values; actual values may be even lower. The G9R (SEQ ID NO: 38) and V39R (SEQ ID NO: 43) isoforms are particularly active, with the Q5M (SEQ ID NO: 22) and G16M (SEQ ID NO: 25) isoforms also showing enhanced activity.

EXAMPLE 5

Rs-AFP2/G9R (SEQ ID NO: 38) and Rs-AFP2/V39R (SEQ ID NO: 43) isoforms: further tests of antifungal activity Isoforms Rs-AFP2/G9R and Rs-AFP2/V39R were subjected to further tests as their antifungal activity in SMF+, in contrast with that of other isoforms, was approximately two-fold higher than that of wild-type Rs-AFP2. Their antifungal activity was determined in SMF with increasing $Ca^{2+}$ or $K^{+}$ concentration and compared with that of plant-derivable wild type Rs-AFP2 (isolated from seed) as well as yeast purified Rs-AFP2. FIG. 7 is a graph of the percentage growth inhibition of *F culmorum* caused by 10 μg/ml of yeast-purified Rs-AFP2 (SEQ ID NO: 20) (open circles), seed-purified Rs-AFP2 (SEQ ID NO: 77) (closed circles), Rs-AFP2/G9R (SEQ ID NO: 38) (squares) and Rs-AFP2/V39R (SEQ ID NO: 43) (triangles) in a medium consisting of SMF with varying concentrations of $CaCl_2$ (panel A) and KCl (panel B).

As shown in FIG. 7, the antifungal activity of yRS-AFP2/G9R and yRS-AFP2/V39R was less reduced by the presence of cations in the growth medium than the activity of wild-type Rs-AFP2. At a concentration of 10 μg/ml, both G9R and V39R caused complete inhibition of the growth of *F culmorum* in the presence of 5 mM $CaCl_2$ whereas wild type Rs-AFP2 was basically inactive under the same conditions. At 10 μg/ml, wild-type Rs-AFP2 was fully active against *F culmorum* only when the $CaCl_2$ concentration was equal to or lower than 1.25 mM. Similarly, the activity of wild type Rs-AFP2 was drastically reduced in the presence of 100 mM KCl, whereas Rs-AFP2 isoforms G9R and V39R were still fully inhibitory to fungal growth.

Thus the G9R and V39R Rs-AFP2 isoforms show no increased activity in the low ionic strength medium, but their activity is more resistant to the presence of cations in comparison with wild-type Rs-AFP2. As relatively high ionic strength conditions occur in all cell compartments, such Rs-AFP2 isoforms displaying a decreased cation antagonism may be useful for plant transformation to obtain disease resistant crops. An Rs-AFP2 isoform yRs-AFP2/G9R/V39R having a mutation at both position 9 (glycine to arginine) and at position 39 (valine to arginine) would carry a net +2 positive charge compared to Rs-AFP2 and is expected to show antifungal activity having an increased salt-tolerence above that even of the individual isoforms G9R or V39R.

The antifungal activity of the G9R and V39R Rs-AFP2 isoforms, was also assessed on a set of seven different phytopathogenic fungi in three media differing in ionic strength: SMF–, SMF plus 1 mM $CaCl_2$ and 50 mM KCl, and SMF plus 5 mM $CaCl_2$ and 50 mM KCl. The fungi tested were: *Alternaria brassicicola, Ascochyta pisi, Botrytis cinerea, Fusarium culmorum, Nectria haematococca, Phoma betae* and *Verticillium dahliae*. The results are shown in Table 3. All $IC_{50}$ values were recorded after 72 hours of growth except for $IC_{50}$ values on *V dahliae* and *F culmorum* which were determined after 96 hours of growth.

The data in Table 3 show that the relative strength of the Rs-AFP2 isoforms may be dependent on the test organism. The activity of the G9R and V39R isoforms against *A brassicola, A pisi* and *B cinerea* was comparable to the activity of Rs-AFP2, while Rs-AFP2 appeared to be more active against *P betae*. However, on three fungi (*F culmorum, N haematococca* and *V dahliae*) the isoforms Rs-AFP2/G9R and Rs-AFP2/V39R were more active than Rs-AFP2 itself particularly in the SMF media with added salts. For example, in the medium SMF plus 1 mM $CaCl_2$ and 50 mM KCl, Rs-AFP2/G9R was approximately three-fold more active than Rs-AFP2 against these three fungi while Rs-AFP2/V39R was approximately two-fold more active than Rs-AFP2 against *F culmorum* and five-fold more active against *N haematococca* and *V dahliae*. The three fungi against which Rs-AFP2/V39R and Rs-AFP2/G9R are more active than Rs-AFP2 belong to the same family of fungi, Namely the Nectriaceae.

TABLE 3

| | $IC_{50}$ VALUES (μG/ml) | | | | | | | | |
|---|---|---|---|---|---|---|---|---|---|
| | SMF | | | SMF + 1 mM $CaCl_2$/50 mM Kcl | | | SMF + 5 mM $CaCl_2$/50 mM Kcl | | |
| FUNGUS | Rs-AFP2 | G9R | V39R | Rs-AFP2 | G9R | V39R | Rs-AFP2 | G9R | V39R |
| A BRASSICCIOLA | 3.2 | 2.6 | 2.5 | >50 | >50 | 50 | >100 | >100 | >100 |
| A PISI | 1.9 | 1.6 | 2.0 | >50 | >50 | >50 | >100 | >100 | >100 |
| B CINEREA | 1.8 | 1.9 | 1.6 | >50 | >50 | >50 | >100 | >100 | >100 |
| F CULMORUM | 2.1 | 2.2 | 2.2 | 4.6 | 1.5 | 2.3 | 22.0 | 7.2 | 7.0 |
| N HAEMATOCOCCA | 2.0 | 2.0 | 2.1 | 48.0 | 16.0 | 9.0 | >100 | 100 | 62.0 |
| P BETAE | 0.9 | 2.0 | 1.4 | 14.0 | 2.50 | 40.0 | 27.0 | >100 | 70.0 |
| V DAHLIAE | 1.0 | 0.5 | 0.4 | 11.0 | 4.0 | 2.3 | 50.0 | 17.0 | 6.0 |

What is claimed is:

1. An antifungal protein having an amino acid sequence which is at least 80% identical to the amino acid sequence of Rs-AFP2 (SEQ ID NO: 9), wherein said amino acid sequence of said antifungal protein contains at least one amino acid selected from the group consisting of a basic residue at the position corresponding to position 9 in Rs-AFP2 (SEQ ID NO: 9), a basic residue at the position corresponding to position 39 in Rs-AFP2 (SEQ ID NO: 9), a hydrophobic residue at the position corresponding to position 5 in Rs-AFP2 (SEQ ID NO: 9) and a hydrophobic residue other than glycine at the position corresponding to position 16 in Rs-AFP2 (SEQ ID NO: 9).

2. An antifungal protein having an amino acid sequence selected from the group consisting of Rs-AFP2 (SEQ ID NO: 9), wherein said amino acid sequence contains at least one mutation selected from the group consisting of a basic residue at the position corresponding to position 9 in Rs-AFP2, a basic residue at the position corresponding to position 39 in Rs-AFP2 (SEQ ID NO: 9), a hydrophobic residue at the position corresponding to position 5 in Rs-AFP2 (SEQ ID NO: 9) and a hydrophobic residue other than glycine at the position corresponding to position 16 in Rs-AFP2 (SEQ ID NO: 9).

3. The antifungal protein of claim 1 wherein said amino acid sequence of said antifungal protein contains at least two amino acids selected from the group consisting of a basic residue at the position corresponding to position 9 in RsAFP-2, a basic residue at the position corresponding to position 39 in Rs-AFP2 (SEQ ID NO: 9), a hydrophobic residue at the position corresponding to position 5 in Rs-AFP2 (SEQ ID NO: 9) and a hydrophobic residue other than glycine at the position corresponding to position 16 in Rs-AFP2 (SEQ ID NO: 9).

4. The antifungal protein of claim 3 wherein said amino acid sequence of said antifungal protein has arginine at the position corresponding to position 9 in RsAFP2 (SEQ ID NO: 9) and arginine at the position corresponding to position 39 in RsAFP2 (SEQ ID NO: 9).

5. An antifungal peptide having at least six amino acid residues identical to a run of amino acid residues in an antifungal protein according to claim 1, said run of residues including at least one of the mutated residues.

* * * * *